(12) United States Patent
Davies et al.

(10) Patent No.: US 9,795,640 B2
(45) Date of Patent: Oct. 24, 2017

(54) CONTROLLING APPETITE, PROMOTING WEIGHT LOSS, REDUCING BODY FAT, AND/OR IMPROVING GLUCOSE TOLERANCE

(71) Applicant: VANDERBILT UNIVERSITY, Nashville, TN (US)

(72) Inventors: Sean S. Davies, Nashville, TN (US); Zhongyi Chen, Nashville, TN (US); Lilu Guo, Nashville, TN (US); Yongqin Zhang, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 196 days.

(21) Appl. No.: 14/345,906

(22) PCT Filed: Sep. 19, 2012

(86) PCT No.: PCT/US2012/056110
§ 371 (c)(1),
(2) Date: Mar. 19, 2014

(87) PCT Pub. No.: WO2013/043719
PCT Pub. Date: Mar. 28, 2013

(65) Prior Publication Data
US 2014/0219965 A1    Aug. 7, 2014

Related U.S. Application Data

(60) Provisional application No. 61/536,238, filed on Sep. 19, 2011.

(51) Int. Cl.
| | |
|---|---|
| *A61K 35/74* | (2015.01) |
| *A61K 38/14* | (2006.01) |
| *A61K 45/06* | (2006.01) |
| *A61K 31/4164* | (2006.01) |
| *A61K 31/43* | (2006.01) |
| *A61K 31/496* | (2006.01) |
| *A61K 31/7036* | (2006.01) |
| *A61K 31/7048* | (2006.01) |
| *A61K 35/745* | (2015.01) |
| *A61K 38/45* | (2006.01) |
| *A61K 38/46* | (2006.01) |
| *A61K 35/744* | (2015.01) |
| *A61K 36/064* | (2006.01) |

(52) U.S. Cl.
CPC .......... *A61K 35/74* (2013.01); *A61K 31/4164* (2013.01); *A61K 31/43* (2013.01); *A61K 31/496* (2013.01); *A61K 31/7036* (2013.01); *A61K 31/7048* (2013.01); *A61K 35/744* (2013.01); *A61K 35/745* (2013.01); *A61K 36/064* (2013.01); *A61K 38/14* (2013.01); *A61K 38/45* (2013.01); *A61K 38/465* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2004/0132819 A1* | 7/2004 | Auestad et al. | 514/560 |
| 2005/0154064 A1 | 7/2005 | Piomelli | |
| 2007/0060648 A1* | 3/2007 | Muller et al. | 514/547 |
| 2010/0074872 A1 | 3/2010 | Blaser | |
| 2010/0143937 A1* | 6/2010 | Peppard et al. | 435/7.1 |
| 2010/0172874 A1 | 7/2010 | Turnbaugh et al. | |

OTHER PUBLICATIONS

Harris, K., Kassis, A., Major, G. & Chou, C.J. Is the Gut Microbiota a New Factor Contributing to Obesity and Its Metabolic Disorders? Journal of Obesity 2012(2012).
Wang, Z., et al. Gut flora metabolism of phosphatidylcholine promotes cardiovascular disease. Nature 472, 57-63 (2011).
Turnbaugh, P.J., et al. An obesity-associated gut microbiome with increased capacity for energy harvest. Nature 444, 1027-1031 (2006).
Turnbaugh, P.J., et al. A core gut microbiome in obese and lean twins. Nature 457, 480-484 (2009).
Vijay-Kumar, M., et al. Metabolic syndrome and altered gut microbiota in mice lacking Toll-like receptor 5. Science 328, 228-231 (2010).
Cani, P.D., et al. Changes in gut microbiota control metabolic endotoxemia-induced inflammation in high-fat diet induced obesity and diabetes in mice. Diabetes 57, 1470-1481 (2008).
Membrez, M., et al. Gut microbiota modulation with norfloxacin and ampicillin enhances glucose tolerance in mice. FASEB J 22, 2416-2426 (2008).
Fu, J., et al. Food intake regulates oleoylethanolamide formation and degradation in the proximal small intestine. J Biol Chem 282, 1518-1528 (2007).
Hansen, H.S. & Diep, T.A. N-acylethanolamines, anandamide and food intake. Biochem Pharmacol 78, 553-560 (2009).
Petersen, G., et al. Intestinal levels of anandamide and oleoylethanolamide in food-deprived rats are regulated through their precursors. Biochim Biophys Acta 1761, 143-150; discussion 141-142 (2006).
Schwartz, G.J., et al. The lipid messenger OEA links dietary fat intake to satiety. Cell Metab 8, 281-288 (2008).
Rodriguez de Fonseca, F., et al. An anorexic lipid mediator regulated by feeding. Nature 414, 209-212 (2001).
Nielsen, M.J., Petersen, G., Astrup, A. & Hansen, H.S. Food intake is inhibited by oral oleoylethanolamide. J Lipid Res 45, 1027-1029 (2004).

(Continued)

*Primary Examiner* — J. Hines
*Assistant Examiner* — Khatol Shahnan Shah
(74) *Attorney, Agent, or Firm* — Stites & Harbison PLLC; Mandy Wilson Decker; Rachel Rutledge

(57) ABSTRACT

A method for treating obesity, insulin sensitivity, and related conditions involves administering to the subject a bacterium for overexpressing a N-acyl-phosphatidylethanolamine (NAPE) and/or a N-acylethanolamine (NAE). A composition includes a bacterium for overexpressing a N-acyl-phosphatidylethanolamine (NAPE) and/or a N-acylethanolamine (NAE); and an ingestible vehicle in which the bacterium is provided.

8 Claims, 21 Drawing Sheets

(56) References Cited

OTHER PUBLICATIONS

Terrazzino, S., et al. Stearoylethanolamide exerts anorexic effects in mice via down-regulation of liver stearoyl-coenzyme A desaturase-1 mRNA expression. FASEB J 18, 1580-1582 (2004).

Gillum, M.P., et al. N-acylphosphatidylethanolamine, a gut-derived circulating factor induced by fat ingestion, inhibits food intake. Cell 135, 813-824 (2008).

Srisai, D., et al. Characterization of the hyperphagic response to dietary fat in the MC4R knockout mouse. Endocrinology 152, 890-902 (2011).

Guzman, M., et al. Oleoylethanolamide stimulates lipolysis by activating the nuclear receptor peroxisome proliferator-activated receptor alpha (PPAR-alpha). J Biol Chem 279, 27849-27854 (2004).

Fu, J., Oveisi, F., Gaetani, S., Lin, E. & Piomelli, D. Oleoylethanolamide, an endogenous PPAR-alpha agonist, lowers body weight and hyperlipidemia in obese rats. Neuropharmacology 48, 1147-1153 (2005).

Fu, J., et al. Oleylethanolamide regulates feeding and body weight through activation of the nuclear receptor PPAR-alpha. Nature 425, 90-93 (2003).

Lo Verme, J., et al. The nuclear receptor peroxisome proliferator-activated receptor-alpha mediates the anti-inflammatory actions of palmitoylethanolamide. Mol Pharmacol 67, 15-19 (2005).

Overton, H.A., et al. Deorphanization of a G protein-coupled receptor for oleoylethanolamide and its use in the discovery of small-molecule hypophagic agents. Cell Metab 3, 167-175 (2006).

Lauffer, L.M., Iakoubov, R. & Brubaker, P.L. GPR119 Is Essential for Oleoylethanolamide-Induced Glucagon-Like Peptide-1 Secretion From the Intestinal Enteroendocrine L-Cell. Diabetes 58, 1058-1066 (2009).

Thabuis, C., et al. Lipid transport function is the main target of oral oleoylethanolamide to reduce adiposity in high-fat-fed mice. J Lipid Res 52, 1373-1382 (2011).

Faure, L., et al. Discovery and characterization of an Arabidopsis thaliana N-acylphosphatidylethanolamine synthase. J Biol Chem 284, 18734-18741 (2009).

Guo, L, Amarnath, V. & Davies, S.S. A liquid chromatography-tandem mass spectrometry method for measurement of N-modified phosphatidylethanolamines. Anal Biochem 405, 236-245 (2010).

Bulat, E. & Garrett, T.A. Putative N-acylphosphatidylethanolamine synthase from Arabidopsis thaliana is a lysoglycerophospholipid acyltransferase. J Biol Chem 286, 33819-33831 (2011).

Horn, C.C., De Jonghe, B.C., Matyas, K. & Norgren, R. Chemotherapy-induced kaolin intake is increased by lesion of the lateral parabrachial nucleus of the rat. Am J Physiol Regul Integr Comp Physiol 297, R1375-1382 (2009).

Hansen, H.H., Hansen, S.H., Schousboe, A. & Hansen, H.S. Determination of the phospholipid precursor of anandamide and other N-acylethanolamine phospholipids before and after sodium azide-induced toxicity in cultured neocortical neurons. J Neurochem 75, 861-871 (2000).

Fu, J., Kim, J., Oveisi, F., Astarita, G., and Piomelli, D. (2008) Targeted enhancement of oleoylethanolamide production in proximal small intestine induces across-meal satiety in rats, Am J Physiol Regul Integr Comp Physiol 295, R45-50.

Jin, X. H., Okamoto, Y., Morishita, J., Tsuboi, K., Tonai, T., and Ueda, N. (2007) Discovery and characterization of a Ca2+-independent phosphatidylethanolamine N-acyltransferase generating the anandamide precursor and its congeners, J Biol Chem 282, 3614-3623.

Jin, X. H., Uyama, T., Wang, J., Okamoto, Y., Tonai, T., and Ueda, N. (2009) cDNA cloning and characterization of human and mouse Ca(2+)-independent phosphatidylethanolamine N-acyltransferases, Biochim Biophys Acta 1791, 32-38.

Lo Verme, J., Gaetani, S., Fu, J., Oveisi, F., Burton, K., and Piomelli, D. (2005) Regulation of food intake by oleoylethanolamide, Cell Mol Life Sci 62, 708-716.

Lionel Faure, Denis Coulon, Jeanny Laroche-Traineau, Marina Le Guedard, Jean-Marie Schmitter, Eric Testet, René Lessire, and Jean-Jacques Bessoule, "Discovery and Characterization of an Arabidopsis thaliana N-Acylphosphatidylethanolamine Synthase" J. Biol. Chem. 2009 284: 18734-18741.

Uyama, T.; Ikematsu, N.; Inoue, M.; Shinohara, N.; Jin, X-H; Tsuboi, K; Tonai, T.; Tokumura, A.; and Ueda, N. (2012) Generation of N-Acylphosphatidylethanolamine by Members of the Phospholipase A/Acyltransferase (PLA/AT) Family, Journal of Biological Chemistry 287, 31905-31919.

Geurts, et al. (2011); Altered gut microbiota and endocannabinoid system tone in obese and diabetic leptin-resistant mice: impact on apelin regulation in adipose tissue; Frontiers in Microbiology; Jul. 2011; 2(149); pp. 1-17.

Covasa (2010) Deficits in gastrointestinal responses controlling food intake and body weight; Am. J. Physiol. Regul. Integr. Comp. Physiol.; 2010; R1423-R1439.

Lucanic, et al.; N-acylethanolamine signalling mediates the effect of diet on lifespan in Caenorhabditis elegans; (2011) Nature; pp. 226-331.

Artman, et al.; Influence of dietary fatty acids on endocannabinoid and N-acylethanolamine levels in rat brain, liver and small intestine; (2008) Biochimica et Biophysics Acta.; pp. 200-212.

* cited by examiner

A.

B.

Water only    pNAPE-EcN

A.

B.

CONTROLLING APPETITE, PROMOTING WEIGHT LOSS, REDUCING BODY FAT, AND/OR IMPROVING GLUCOSE TOLERANCE

RELATED APPLICATIONS

This application claims priority from U.S. Provisional Application Ser. No. 61/536,238 filed Sep. 19, 2011, the entire disclosure of which is incorporated herein by this reference.

GOVERNMENT INTEREST

This invention was made with government support under grant numbers DP2 OD003137, DK59637, DK20593, and UL1RR024975-01 awarded by the National Institutes of Health. The government has certain rights in the invention.

TECHNICAL FIELD

The presently-disclosed subject matter relates to compositions and methods for treating obesity and/or insulin sensitivity. In particular, the presently-disclosed subject matter relates to use of bacteria for overexpressing an N-acyl-phosphatidylethanolamine (NAPE) and/or or a N-acylethanolamine (NAE) for such treatment.

INTRODUCTION

Obesity and excess weight/body fat are well-known risk factors for a variety of diseases including diabetes and cardiovascular diseases. Obesity is increasing at an alarming rate in Westernized Countries. For example, in excess of 30% of individuals are considered obese in some regions of the United States, representing an exponential increase over the last decade.

Current treatments for obesity and overweight conditions focus on caloric restriction and increased physical activity. While such treatment programs can work for some individuals, whether due to poor adherence or otherwise, they are ineffective for much of the population. Current treatments also include bariatric surgery, which is an invasive and risky procedure that is reserved for extreme circumstances. While as number of pharmaceuticals and been used in treatment programs, many have undesirable side effects and/or limited efficacy.

Accordingly, there remains a need in the art for a compositions and methods to effectively treat obesity, excess weight/body fat, and related conditions.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Disorders including obesity, diabetes, and cardiovascular disease have become widespread in Westernized nations. The composition of an individual's gut microbiota is a significant determinant of their susceptibility to these metabolic diseases.[1-7] The present inventors contemplated that appropriately modifying this microbiota can ameliorate disease. Herein, the present inventors disclose a strategy to remodel the gut microbiota to include bacteria genetically modified to express therapeutic factors that protect against development of obesity. For instance, N-acylphosphatidylethanolamines (NAPEs) are precursors to a family of anorexic lipids, the N-acylethanolamines (NAEs), that are normally synthesized in the proximal small intestine in response to feeding[8] and that markedly reduce food intake and obesity[9-11].

As disclosed herein, administration of bacteria genetically modified to express NAPEs and/or NAEs protected against obesity, notwithstanding animals receiving a high fat diet. Animals receiving these modified bacteria in their drinking water had significantly lower food intake, adiposity, insulin resistance, and liver steatosis compared to mice receiving standard drinking water, vehicle or unmodified bacteria. It was found that the protective effects of these modified bacteria persisted for at least four weeks after cessation of their administration. The results demonstrate that remodeling gut microbiota to include appropriately modified bacteria can be an effective strategy for treating metabolic diseases.

NAPEs are hydrolyzed in the intestine to NAEs and intraperitoneal administration of either NAPEs or NAEs with saturated or monounsaturated N-acyl chains such as N-palmitoyl-ethanolamide (PEA). N-stearoyl-ethanolamide (SEA) and N-oleoyl-ethanolamide (OEA) markedly reduces food intake[12-16] and obesity in animals fed a high-fat diet[15-18]. NEAs activate PPARα[17,19,20] and genetic ablation of PPARα significantly blunts their anorectic effects[19]. Additionally, NAEs activate GPR119[21], which in intestinal L-cells triggers glucagon-like peptide-1 (GLP-1) secretion[22]. Inhibition of lipid transport also appears to contribute to the reduced food intake and obesity induced by NAEs[23].

The presently-disclosed subject matter includes a method for treating obesity, insulin sensitivity, and related conditions, which involves administering to a subject a bacterium for overexpressing a N-acyl-phosphatidylethanolamine (NAPE) and/or a N-acylethanolamine (NAE).

The presently-disclosed subject matter also includes a composition, which includes a bacterium for overexpressing a N-acyl-phosphatidylethanolamine (NAPE) and/or N-acylethanolamine (NAE); and an ingestible vehicle in which the bacterium is provided.

In some embodiments of the presently-disclosed subject matter, the bacterium overexpresses NAPE. In some embodiments, the NAPE overexpressed is selected from one or more of the NAPEs in the following group: $C_{16:0}$NAPE, $C_{16:1}$NAPE, $C_{17cy}$NAPE, $C_{18:0}$NAPE, $C_{18:1}$NAPE, and $C_{18:2}$NAPE. In some embodiments, the NAPE overexpressed is selected from one or more of the NAPEs in the following group: $C_{16:0}$NAPE, $C_{16:1}$NAPE, and $C_{18:1}$NAPE. In some embodiments, the NAPE overexpressed is selected from one or more of the NAPEs in the following group: $C_{16:0}$NAPE and $C_{18:1}$NAPE.

In some embodiments of the presently-disclosed subject matter, the bacterium overexpresses NAE. In some embodiments, the NAE overexpressed is selected from one or more of the NAEs in the following group: $C_{16:0}$NAE, $C_{16:1}$NAE, $C_{17cy}$NAE, $C_{18:0}$NAE, $C_{18:1}$NAE, $C_{18:2}$NAE, $C_{20:4}$NAE, and $C_{22:6}$NAE. In some embodiments, the NAE overexpressed is selected from one or more of the NAEs in the following group: $C_{16:0}$NAE, $C_{16:1}$NAE, $C_{17cy}$NAE, and $C_{18:1}$NAE. In some embodiments, the NAE overexpressed is $C_{16:1}$NAE.

In some embodiments of the presently-disclosed subject matter, the bacterium is transfected with a vector comprising a nucleic acid encoding an enzyme for synthesizing NAPE and/or NAE. In some embodiments, the enzyme is selected from a NAPE acyltransferase, and a NAPE-phospholipase D (NAPE-PLD). In some embodiments, the enzyme is selected from a member of the HRAS-like suppressor family 1-5 (HRASLS1-5) that have been shown to be mammalian N-acyltransferases, and which are also known as phospholipase A/acyltransferase 1-5 (PLA/AT-1-5). In some embodiments, the enzyme is a phospholipase that converts NAPE to NAE, e.g., a mammalian or yeast phospholipase that converts NAPE to NAE. In some embodiments, the bacterium is transfected with one or more vectors comprising nucleic acids encoding at least two enzymes selected from NAPE acyltransferase, and NAPE-phospholipase D (NAPE-PLD). In some embodiments, the vector includes a promoter that can be recognized by endogenous *E. coli* polymerase. In some embodiments, a lac Z operator has been removed. In some embodiments, the vector includes a T5 promoter.

In some embodiments of the presently-disclosed subject matter, the bacterium is a biosafety level 1 bacterium capable of colonizing in the gut of a subject. In some embodiments, the bacterium is a gram negative bacterium. In some embodiments, the bacterium is a gram positive bacterium. In some embodiments, the bacterium is an entric bacterium. In some embodiments, the bacterium is selected from *Bacillus, Bifidobacterium, Bacteroidetes, Lactobacillus, Lactoccus, Enterobacteriaceae, Escherichium*, and *Saccharomyces*. In some embodiments, the bacterium is *E. coli*. In some embodiments, the bacterium is *Bifidobacteria*.

As disclosed herein, in some embodiments, the bacterium can be provided in an ingestible vehicle. In some embodiments, the ingestible vehicle is selected from: a beverage, a food product, a capsule, granules, and tablets. In some embodiments, the ingestible vehicle is selected from: mile, water, water-based beverage, yogurt, candy, gum, and gelatin. In some embodiments, the ingestible vehicle is water including gelatin. In some embodiments, the ingestible vehicle is water including gelatin and filler.

In some embodiments, methods disclosed herein further involve administering an antibiotic treatment prior to administering the bacterium. In some embodiments, methods disclosed herein further involve administering an antibiotic treatment prior to administering the bacterium. In some embodiments, the antibiotic can be selected from ampicillin, amphotericin-B, kanamycin, metronidazole, neomycin, norfloxacin, vancomycin, and mixtures thereof. In some embodiments, the antibiotic is ampicillin, norfloxacin, and/or kanamycin. In some embodiments, the antibiotic is norfloxacin, and/or kanamycin. In some embodiments, the antibiotic is ampicillin.

In some embodiments, methods disclosed herein administering multiple doses of the bacterium. In some embodiments, the bacterium is administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days. In some embodiments, the bacterium is administered every 1, 2, 3, 4, 5, 6, 7, 8, 9, 10, 11, 12, 13, 14, or 15 weeks. In some embodiments, the bacterium is administered every 4 weeks. In some embodiments, the bacterium is administered every 6 weeks. In some embodiments, the bacterium is administered every 12 weeks.

The presently-disclosed subject matter further includes a kit. In some embodiments the kit includes a bacterium for overexpressing a N-acyl-phosphatidylethanolamine (NAPE) and/or a N-acylethanolamine (NAE), as described hereinabove, and an antibiotic. In some embodiments the kit includes a composition, as described hereinabove, and an antibiotic.

In some embodiments, the kit includes a first bacterium for overexpressing a NAPE, or a first composition including the first bacterium; and a second bacterium for overexpressing NAE, or a second composition including the second bacterium.

In some embodiments, the kit includes multiple doses of a bacterium or composition, as described hereinabove. Embodiments of the kit can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 doses of the bacterium or composition.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1A:
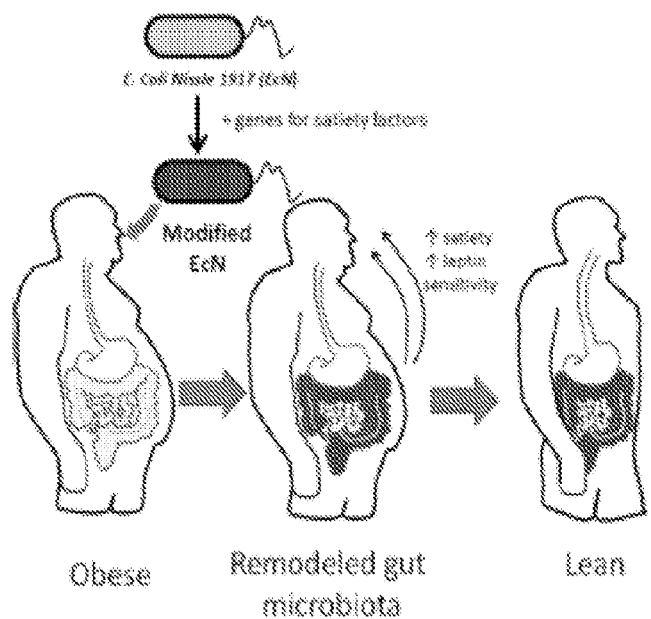
FIG. 1A. Schematic of proposed strategy for treating obesity by remodeling gut microbiota with bacteria therapeutically-modified to secrete anorexigenic factors.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods, compositions, and kits useful for treating conditions associated with obesity, excess weight or body fat, and/or high body mass index (BMI). As used herein, and for purposes of avoiding unnecessary repetition, treating obesity and/or insulin sensitivity is inclusive of: controlling appetite, controlling food intake, controlling weight, controlling body fat mass, controlling BMI, reducing weight, reducing body fat mass/adiposity, treating obesity, controlling obesity, preventing obesity, treating livers steatosis, controlling liver steatosis, reducing liver steatosis, improving glucose tolerance, maintaining insulin sensitivity, treating insulin resistance, and treating conditions for which obese subjects are at an increased risk, including but not limited to diabetes and cardiovascular diseases, such as coronary heart disease and stroke.

As used herein, the terms "treatment" or "treating" relate to curing or substantially curing a condition, as well as ameliorating at least one symptom of the condition, and are inclusive of prophylactic treatment and therapeutic treatment. As would be recognized by one or ordinary skill in the art, treatment that is administered prior to clinical manifestation of a condition then the treatment is prophylactic (i.e., it protects the subject against developing the condition). If the treatment is administered after manifestation of the condition, the treatment is therapeutic (i.e., it is intended to diminish, ameliorate, control, stabilize, or maintain the existing condition and/or side effects associated with the condition).

The presently-disclosed subject matter includes a method for treating a subject, which involves administering to the subject a bacterium for overexpressing a N-acyl-phosphatidylethanolamine (NAPE) and/or a N-acylethanolamine (NAE).

The administration can be appropriate for directing the bacterium to the gut (intestine, stomach, etc.) of the subject. In this regard, oral administration is contemplated. The administration can be of an effective amount of the bacterium. As used herein, the terms "effective amount" and "therapeutically effective amount" are used interchangeably and mean a dosage sufficient to provide treatment for the condition being treated. This can vary depending on the patient, the condition, and the treatment being effected. The exact amount that is required will vary from subject to subject, depending on the species, age, and general condition of the subject, the particular carrier or vehicle being used, and the like. As such, the effective amount will vary based on the particular circumstances, and an appropriate effective amount can be determined in a particular case by one of ordinary skill in the art using only routine experimentation.

As will be recognized by those skilled in the art upon study of this application, various NAPEs and NAEs can be overexpressed in accordance with the presently disclosed subject matter. A non-exhaustive list of examples of NAPEs that can be expressed includes: $C_{16:0}$NAPE, $C_{16:1}$NAPE, $C_{17cy}$NAPE, $C_{18:0}$NAPE, $C_{18:1}$NAPE, and $C_{18:2}$NAPE. A non-exhaustive list of examples of NAPES that can be expressed includes: $C_{16:0}$NAE (palmitoylethanolamide), $C_{16:1}$NAE, $C_{17cy}$NAE, $C_{18:0}$NAE (stearoylethanolamide), $C_{18:1}$NAE (oleylethanolamide), $C_{18:2}$NAE, $C_{20:4}$NAE (anandamide), and $C_{22:6}$NAE. Further relevant information can be found, for example, in Gillum (2008)[15], Srisai (2011)[16], Rodriguez de Fonseca (2001)[12], and Hansen (2009)[9], which are which are incorporated herein by this reference.

As will be recognized by one of ordinary skill in the art, overexpressing NAPE can be achieved by expression of an enzyme that can synthesize NAPE, such that NAPEs are present in greater concentrations than they would be absent the expression of the enzyme. Similarly, as will be recognized by one of ordinary skill in the art, overexpressing NAE can be achieved by expression of an enzyme that can synthesize NAE, such that NAEs are present in greater concentrations than they would be absent the expression of the enzyme.

With reference to the following biosynthesis scheme, a NAPE acyltransferase (sometimes referred to as a NAPE synthase) catalyzes the synthesis of NAPE, and a NAPE-phospholipase D (NAPE-PLD) catalyzes the release of NAE from NAPE.

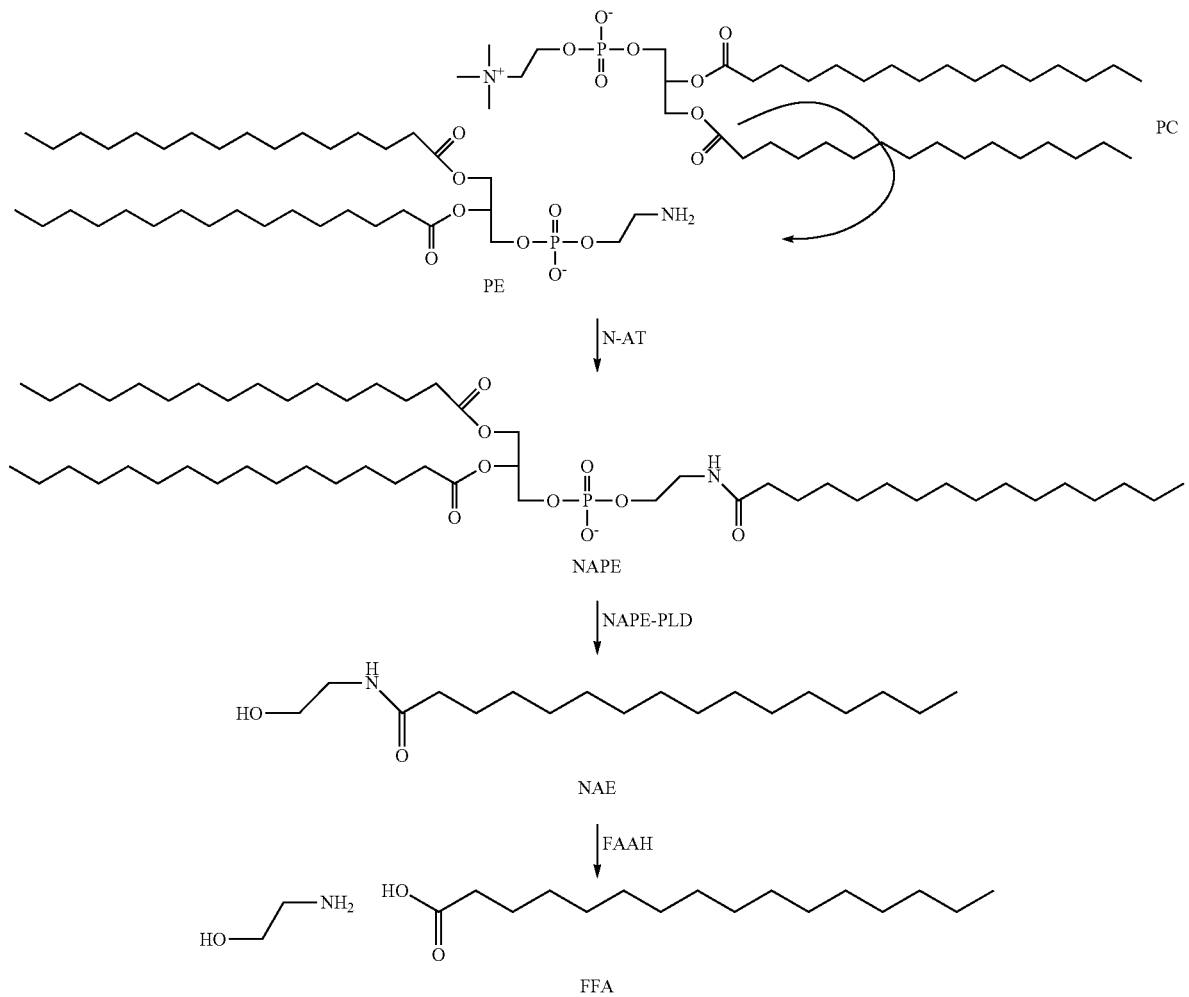

When a bacterium is provided for overexpressing NAPE and/or NAE in accordance with the presently-disclosed subject matter, the bacterium is transfected with a vector comprising a nucleic acid encoding polypeptide for synthesizing NAPE and/or NAE. In some embodiments, a vector comprising nucleic acids encoding more than one polypeptide for synthesizing NAPE and/or NAE can be provided. Examples of such polypeptides, or enzymes, include, but are not limited to, a NAPE acyltransferase (sometimes referred to as a NAPE synthase). NAPE-phospholipase D (NAPE-PLD). Further examples include, but are not limited to, the enzymes encoded by the sequences having the following accession numbers: Gene ID 844205 (for At1g78690), and GenBank: AB255646.1 (for calcium independent N-acyltransferase). Further examples include, but are not limited to, enzyme is selected from a member of the HRAS-like suppressor family 1-5 (HRASLS1-5) that have been shown to be mammalian N-acyltransferases, and which are also known as phospholipase A/acyltransferase 1-5 (PLA/AT-1-5)[34]. Further examples include, but are not limited to, enzymes encoded by the sequences having the following accession numbers: NP_065119 (PLA/AT-1) NM 017878 (PLA/AT-2), AB439591 (PLA/AT-3), NM 004585 (PLA/AT-4), and NM 054108 (PLA/AT-5). Further examples include, but are not limited to a phospholipase that converts NAPE to NAE, e.g., a mammalian or yeast phospholipase that converts NAPE to NAE. See also, Jin (2009)[31] and Uyama (2012)[34], which are incorporated herein by reference. In some embodiments, a functional fragment of the full length enzyme can be expressed.

Some of the polynucleotide and polypeptide sequences disclosed herein are cross-referenced to publicly-available database accession numbers, e.g., GENBANK® accession numbers. The sequences cross-referenced in such databases are expressly incorporated by reference as are equivalent and related sequences present in the databases. Also expressly incorporated herein by reference are all annotations present in the database associated with the sequences/accession numbers disclosed herein. Unless otherwise indicated or apparent, the references to the databases, e.g., GENEBANK® are references to the most recent version of the database as of the filing date of this Application.

The term "nucleic acid" or "nucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res* 19:5081; Ohtsuka et al. (1985) *J Biol Chem* 260:2605-2608; Rossolini et al. (1994) *Mol Cell Probes* 8:91-98). The terms "nucleic acid" or "nucleic acid sequence" can also be used interchangeably with gene, open reading frame (ORF), cDNA, and mRNA encoded by a gene.

The term "isolated nucleic acid" refers to a nucleic acid the structure of which is not identical to that of any naturally occurring nucleic acid or to that of any fragment of a naturally-occurring genomic nucleic acid spanning more than three separate genes. An isolated nucleic acid therefore including, for example, a DNA which has the sequence of part of as naturally-occurring genomic DNA molecule but is not flanked by both of the coding sequences that flank that part of the molecule in the genome of the organism in which it naturally occurs; a nucleic acid incorporated into a vector or into the genomic DNA of a prokaryote or eukaryote in a manner such that the resulting molecule is not identical to any naturally-occurring vector or genomic DNA; a separate molecule such as a cDNA, a genomic fragment, a fragment produced by polymerase chain reaction (PCR), or a restriction fragment; and a recombinant nucleotide sequence that is part of a hybrid gene, i.e., a gene encoding a fusion protein. Specifically excluded from this definition are nucleic acids present in mixtures of (1) DNA molecules, (2) transfected cells, and (3) cell clones, e.g., as these occur in a DNA library such as a cDNA or genomic DNA library.

The term "isolated", when used in the context of an isolated DNA molecule or an isolated polypeptide, is a DNA molecule or polypeptide that, by the hand of man, exists apart from its native environment and is therefore not a product of nature. An isolated DNA molecule or polypeptide can exist in a purified form or can exist in a non-native environment such as, for example, in a transgenic host cell.

The terms "polypeptide", "protein", and "peptide", which are used interchangeably herein, refer to a polymer of the 20 protein amino acids, or amino acid analogs, regardless of its size or function. The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least at least 20, 30, 40 or 50 amino acids long, or at least 100, 150, 200, 300, 500 or more amino acids long. A fragment can also be a "functional fragment," in which the fragment retains a specific biological function of the reference sequence.

As will be apparent to those skilled in the art, an appropriate vector can be used, and can be selected based on the bacterium being employed. In some embodiments, the vector includes a promoter that can be recognized by endogenous *E. coli* polymerase. In some embodiments, the vector includes a T5 promoter. In some embodiments, the expression is induced by IPTG, which leads the repressors to move off the lac operator, freeing up the promoter for the polymerase. In some embodiments, one of the lac Z operators is removed to increase basal activity.

Various bacteria can be employed for practicing the presently-disclosed subject matter. In some embodiments of the presently-disclosed subject matter, the bacterium is a biosafety level 1 bacterium capable of colonizing in the gut of a subject. Without wishing to be bound by theory or mechanism, it is contemplated that gram negative bacteria is better able to transfer NAPE and/or NAE tea host intestinal cells. As such, in some embodiments, the bacterium is a gram negative bacterium. In some embodiments, the bacterium is a gram positive bacterium. In some embodiments, the bacterium is an entric bacterium. In some embodiments, the bacterium is selected from *Bacillus, Bifidobacterium, Bacteroidetes, Lactobacillus, Lactoccus, Enterobacteriaceae, Escherichium*, and *Saccharomyces*. In some embodiments, the bacterium is *E. coli*. In some embodiments, the bacterium is *Bifidobacteria*.

The presently-disclosed subject matter further includes a composition that includes a bacterium for overexpressing a N-acyl-phosphatidylethanolamine (NAPE and/or a N-acylethanolamine (NAE) as described hereinabove, and an ingestible vehicle in which the bacterium is provided.

In some embodiments of the presently-disclosed subject matter, the bacterium can be provided in an ingestible vehicle, appropriate for administration, particularly oral administration, to the subject. Any ingestible vehicle appropriate for delivering a bacterium to a subject as is known to those of ordinary skill in the art can be used. Examples of ingestible vehicles appropriate for use in accordance with the presently-disclosed subject matter include, but are not limited to, beverages, such as milk, and water and water-based beverages, such as, juice, sports drinks, and soft drinks, and including water containing gelatin and/or fiber; food products, such as yogurt and kefir; candies; gums; capsules; granules; gelatin; and tablets.

As noted hereinabove, in some embodiments, methods are provided wherein the bacterium is administered, which is inclusive of a method of administering a composition comprising a bacterium as described herein. In some embodiments, the methods further include administering an antibiotic treatment prior to administering the bacterium and/or composition. The antibiotic can be selected from any appropriate antibiotic as will be recognized by one of ordinary skill in the art upon study of this document. In some embodiments, methods disclosed herein further involve administering an antibiotic treatment prior to administering the bacterium. In some embodiments, the antibiotic can be selected from ampicillin, amphotericin-B, kanamycin, metronidazole, neomycin, norfloxacin, vancomycin, and mixtures thereof. In some embodiments, the antibiotic is ampicillin, norfloxacin, and/or kanamycin. In some embodiments, the antibiotic is norfloxacin, and/or kanamycin. In some embodiments, the antibiotic is ampicillin.

In some embodiments, the antibiotic treatment can be administered in multiple doses or treatments. In some embodiments, the multiple doses can be of the same or of different antibiotics or mixtures thereof. In some embodiments, the multiple doses can be administered at substantially the same time, immediately following one another, or at different time points.

In some embodiments, the antibiotic treatment includes a first treatment including a mixture of vancomycin, neomycin, metronidazole, and amphotericin-B; and a second treatment including ampicillin. In some embodiments, the antibiotic treatment includes a first treatment including a mixture of about 5 mg/ml vancomycin, about 10 mg/ml neomycin, about 10 mg/ml metronidazole, and about 0.1 mg/ml amphotericin-B; and a second treatment including about 1 mg/ml ampicillin.

In some embodiments, the method includes administering multiple doses the bacterium or composition. The doses can each comprise an effective amount of the bacterium. In some embodiments, the multiple doses are administered at regular intervals, as needed. In some embodiments, the bacterium is administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days. In some embodiments, the bacterium is administered every 1, 2, 3, 4, 5, 6, 7, 8, 9, 10, 11, 12, 13, 14, or 15 weeks.

The presently-disclosed subject matter further includes a kit. In some embodiments the kit includes a bacterium for overexpressing a N-acyl-phosphatidylethanolamine (NAPE) and/or a N-acylethanolamine (NAE), as described hereinabove, and an antibiotic. In some embodiments the kit includes a composition, as described hereinabove, and an antibiotic. In some embodiments, the antibiotic is selected from ampicillin, amphotericin-B, kanamycin, metronidazole, neomycin, norfloxacin, vancomycin, and mixtures thereof. In some embodiments, the antibiotic is ampicillin, norfloxacin, and/or kanamycin. In some embodiments, the antibiotic is norfloxacin, and/or kanamycin. In some embodiments, the antibiotic is ampicillin. In some embodiments, the antibiotic treatment includes a first treatment including a mixture of vancomycin, neomycin, metronidazole, and amphotericin-B; and a second treatment including ampicillin. In some embodiments, the antibiotic treatment includes a first treatment including a mixture of about 5 mg/ml vancomycin, about 10 mg/ml neomycin, about 10 mg/ml metronidazole, and about 0.1 mg/ml amphotericin-B; and a second treatment including about 1 mg/ml ampicillin.

In some embodiments, the kit includes a first bacterium for overexpressing a NAPE, or a first composition including the first bacterium; and a second bacterium for overexpressing NAE, or a second composition including the second bacterium.

In some embodiments, the kit includes multiple doses of a bacterium or composition, as described hereinabove. Embodiments of the kit can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 doses of the bacterium or composition.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human or non human. Thus, veterinary therapeutic uses are provided in accordance with the presently disclosed subject matter.

As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to; carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value of to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

Figure 1B:
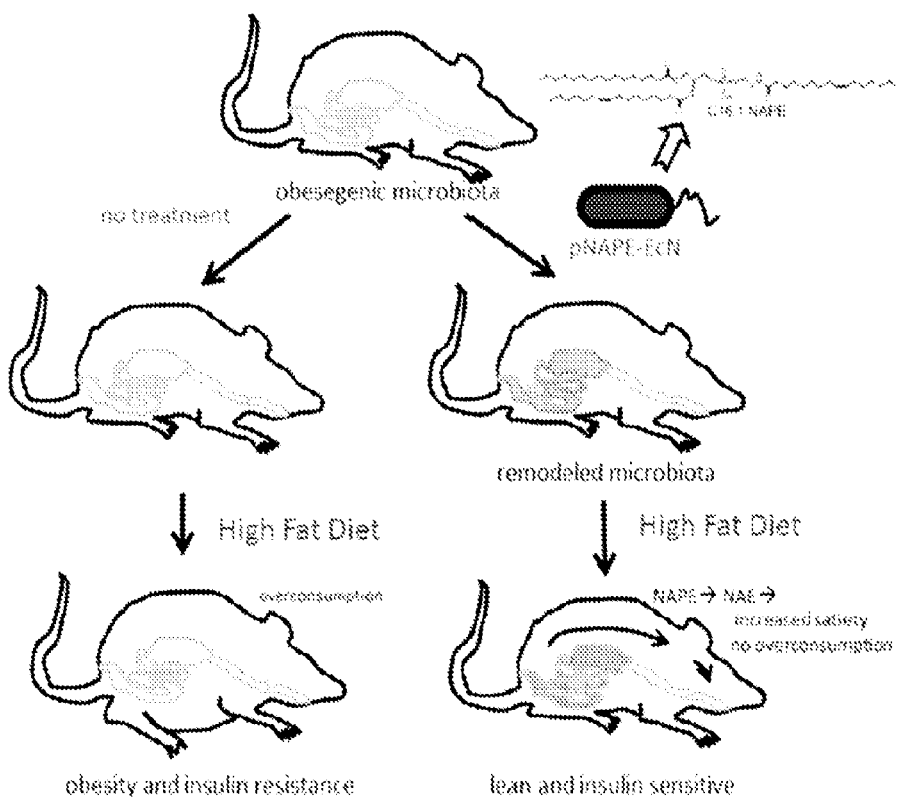
FIG. 1B. Schematic of therapeutic strategy. Administration of pNAPE-EcN, *E. coli* Nissle 1917 genetically modified to synthesized anorexigenic N-acylphosphatidylethanolamines (NAPEs) such as C16:1NAPE, remodels the gut microbiota of C57BL6 mice to include these modified bacteria. NAPEs secreted by pNAPE-EcN are converted by colonic cells to NAEs where they induce neuronal/enterocrine signaling that Normally, when mice are given a high-fat diet, they consume more calories that needed to maintain current fat mass, leading to obesity, insulin resistance, and liver steatosis. The higher levels of NAPEs caused by the presence of pNAPE-EcN in the gut increase satiety and prevent this overconsumption, thereby preventing adiposity and resulting insulin resistance and steatosis.
Figure 2:
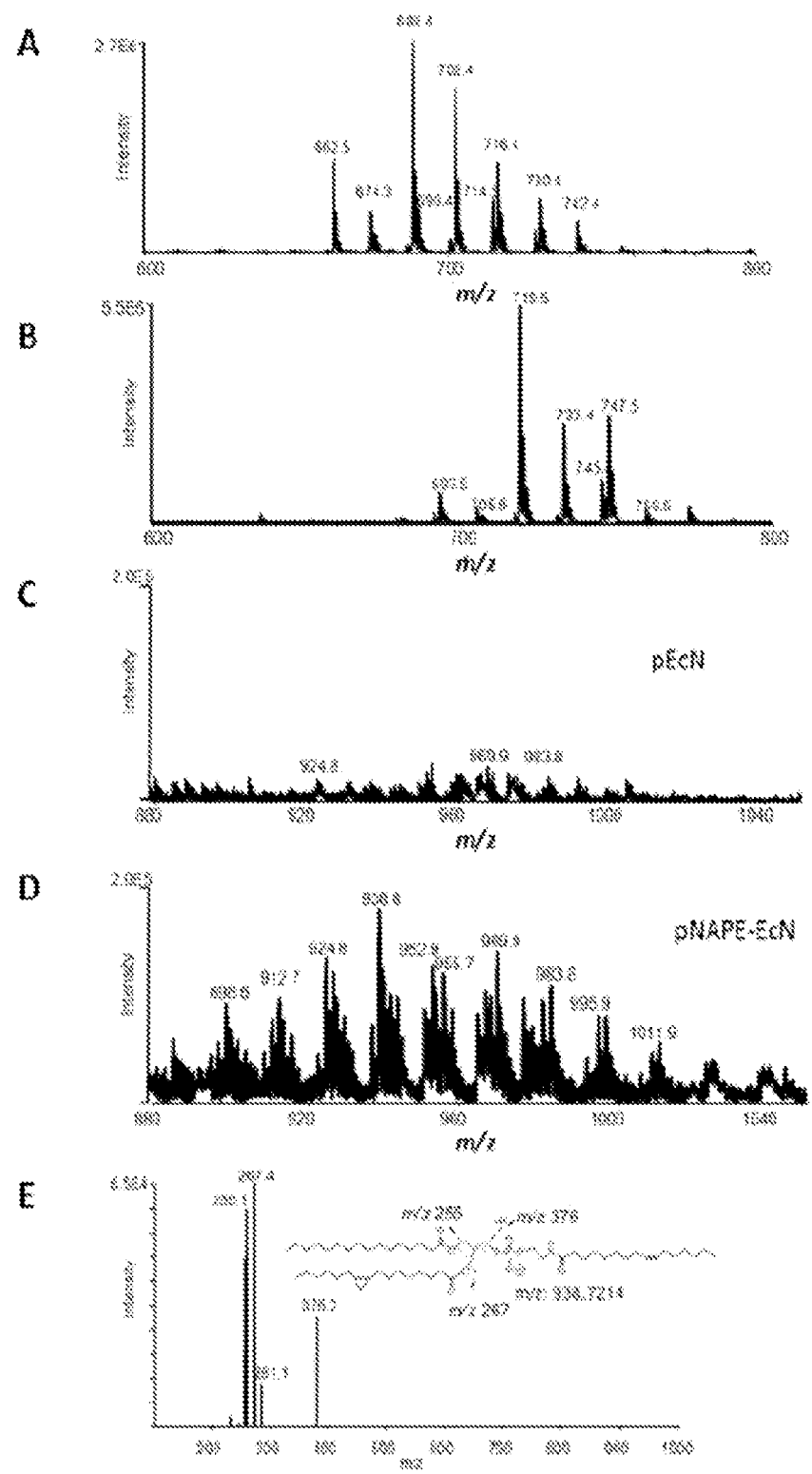
FIG. 2. Identification of major N-acyl phosphatidylethanolamines (NAPE) in pNAPE-EcN by mass spectral analysis. A. Mass spectrum (m/z 600 to 800) from phosphatidylethanolamine (PE) region (Rt 4.5-5.0 min.) of HPLC chromatograph from EcN transformed with vector lacking the At1g78690 gene (pEcN). Identity of each major PE species is given in Table 1. B. Mass spectrum (m/z 600 to 800) from phosphatidylglycerol (PG) region (Rt 3.0-3.3 min) of HPLC chromatograph from pEcN. Identity of each major PG species given in Table 2. C. Mass spectrum (m/z 880 to 1050) from triacyl anionic phospholipid region of HPLC chromatograph from pEcN. Identifications of individual NAPE and acyl-PG species given in Table 1 and Table 2, respectively. D. Same mass spectrum range for pNAPE-EcN. E. Collision Induced Disassociation (CID) spectrum of m/z ion 938.8. Interpretation of product ions are shown in inset.
Figure 3:
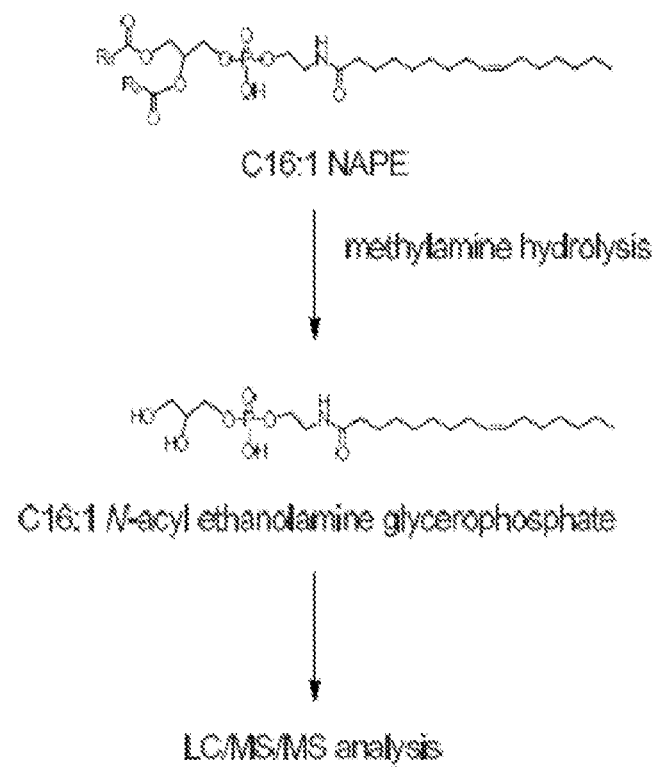
FIG. 3. Transformation of EcN with At1g78690 markedly increases levels of saturated and monounsaturated NAPEs in EcN. Saturated and monounsaturated NAEs are the principal species that have been shown to reduce food intake. A. Schematic of NAPE measurement method. NAPE species with the same N-acyl chain, but different O-acyl chains ($R_1$ and $R_2$ are fatty acids ranging from C14 to C18) were measured as a single N-acyl-ethanolamine glycerophosphate species by LC/MS/MS after deacylation using methylamine B. Levels of individual NAPEs in transformed EcN. Measurements represent mean±s.e.m. for duplicate samples.
Figure 3:
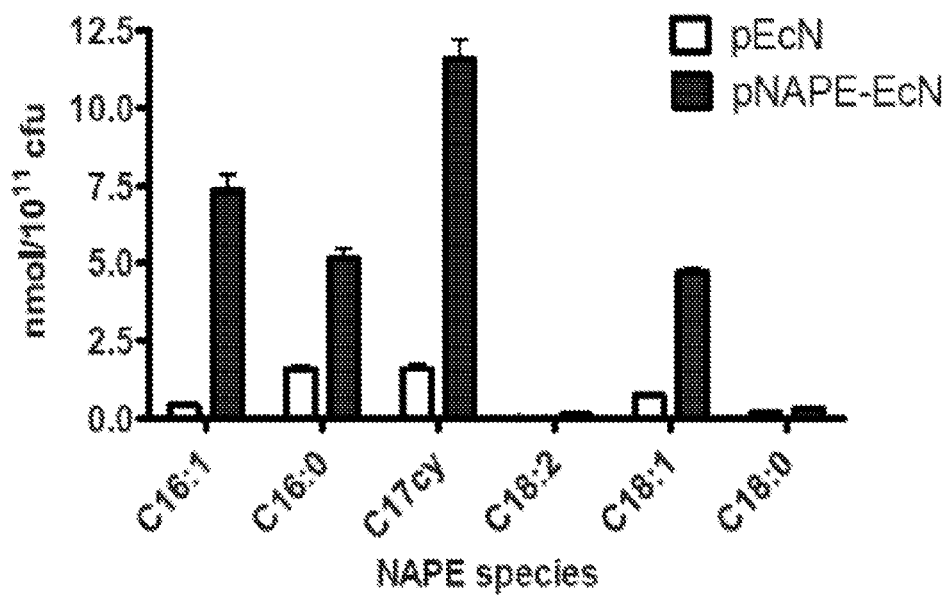

The goal of this study was to determine if administration of gut bacteria genetically modified to biosynthesize NAPE would result in significant changes in intestinal NAPE levels that would reduce food intake and protect against development of obesity when mice were fed a high fat diet (FIG. 1). The C41-DE3 laboratory strain of *E. coli* (Ec) had previously been transformed with At1g78690, an N-acyltransferase from *Arabidopsis thaliana* that catalyzes the synthesis of NAPEs, which markedly increased NAPE levels in these bacteria (pNAPE-Ec) compared to those transformed with empty vector (pEc) 24,25. To facilitate greater colonization and persistence in the gut, the probiotic wild-type strain of *E. coli*, Nissle 1917 (EcN), was also transformed with At1g78690 (pNAPE-EcN). To facilitate monitoring of colonization by transformed EcN, the *P. luminescens* luciferase operon (Lux) was also inserted into the RecA gene of the EcN chromosome. Phospholipid extracts from both pNAPE-EcN and pEcN were analyzed by negative ion mass spectrometry (FIG. 2) and the identified NAPE species were consistent with N-acylation of the major bacterial PE species (Table 1). pNAPE-EcN had markedly higher levels of three NAPEs (C16:1, C16:0, and C18:1NAPE) expected to exert anorexigenic effects (FIG. 3). In addition to these NAPE species, several species with m/z ions consistent with O-acyl-phosphatidylglycerols (acyl-PG) species 26 were also enriched in pNAPE-EcN (Table 2).

TABLE 1

Expected masses for major phosphatidylethanolamine (PE) and N-acyl-PE (NAPE) species in *E. coli Nissle* 1917 transformed with At1g78690p.

| PE species O-acyl chains | Resulting NAPE species N-acyl chain added | | | |
|---|---|---|---|---|
| | unmodified PE | N-C16:1 | N-C16:0 | N-C17c | N-C18:1 |
| C17cy + C16:0 | 702.5 | 938.7 | 940.7 | 952.7 | 966.7 |
| C16:0 + C16:1 | 688.5 | 924.7 | 926.7 | 938.7 | 952.7 |
| C14:0 + C18:1 | 688.5 | 924.7 | 926.7 | 938.7 | 952.7 |
| C16:0 + C16:0 | 690.5 | 926.7 | 928.7 | 940.7 | 954.8 |
| C14:0 + C16:0 | 662.5 | 898.7 | 900.7 | 912.7 | 926.7 |
| C17cy + C18:0 | 730.5 | 966.7 | 968.7 | 980.7 | 994.8 |
| C18:1 + C16:0 | 716.5 | 952.7 | 954.7 | 966.7 | 980.8 |
| C18:0 + C16:1 | 716.5 | 952.7 | 954.7 | 966.7 | 980.8 |
| C18:1 + C16:1 | 714.5 | 950.7 | 952.7 | 964.7 | 978.8 |

TABLE 2

Expected masses for major phosphatidylglycerol (PG) and O-acyl PG (acyl-PG) species in *E.coli Nissle* 1917 transformed with At1g78690p.

| PG species O-acyl chains | Resulting Acyl-PG species O-acyl chain added | | | |
|---|---|---|---|---|
| | Unmodified PG | O-C16:1 | O-C16:0 | O-C17cy | O-C18:1 |
| C17c + C16:0 | 733.5 | 969.7 | 971.7 | 983.7 | 997.7 |
| C16:0 + C16:1 | 719.5 | 955.7 | 957.7 | 969.7 | 983.7 |
| C14:0 + C18:1 | 719.5 | 955.7 | 957.7 | 969.7 | 983.7 |
| C16:0 + C16:0 | 721.5 | 957.7 | 959.7 | 971.7 | 985.7 |
| C14:0 + C16:0 | 693.5 | 929.7 | 931.7 | 943.7 | 957.7 |
| C17c + C18:0 | 761.5 | 997.7 | 999.7 | 1011.7 | 1025.7 |
| C18:1 + C16:0 | 747.5 | 983.7 | 985.7 | 997.7 | 1011.7 |
| C18:0 + C16:1 | 747.5 | 983.7 | 985.7 | 997.7 | 1011.7 |
| C18:1 + C16:1 | 745.5 | 981.7 | 983.7 | 995.7 | 1009.7 |

Figure 4:
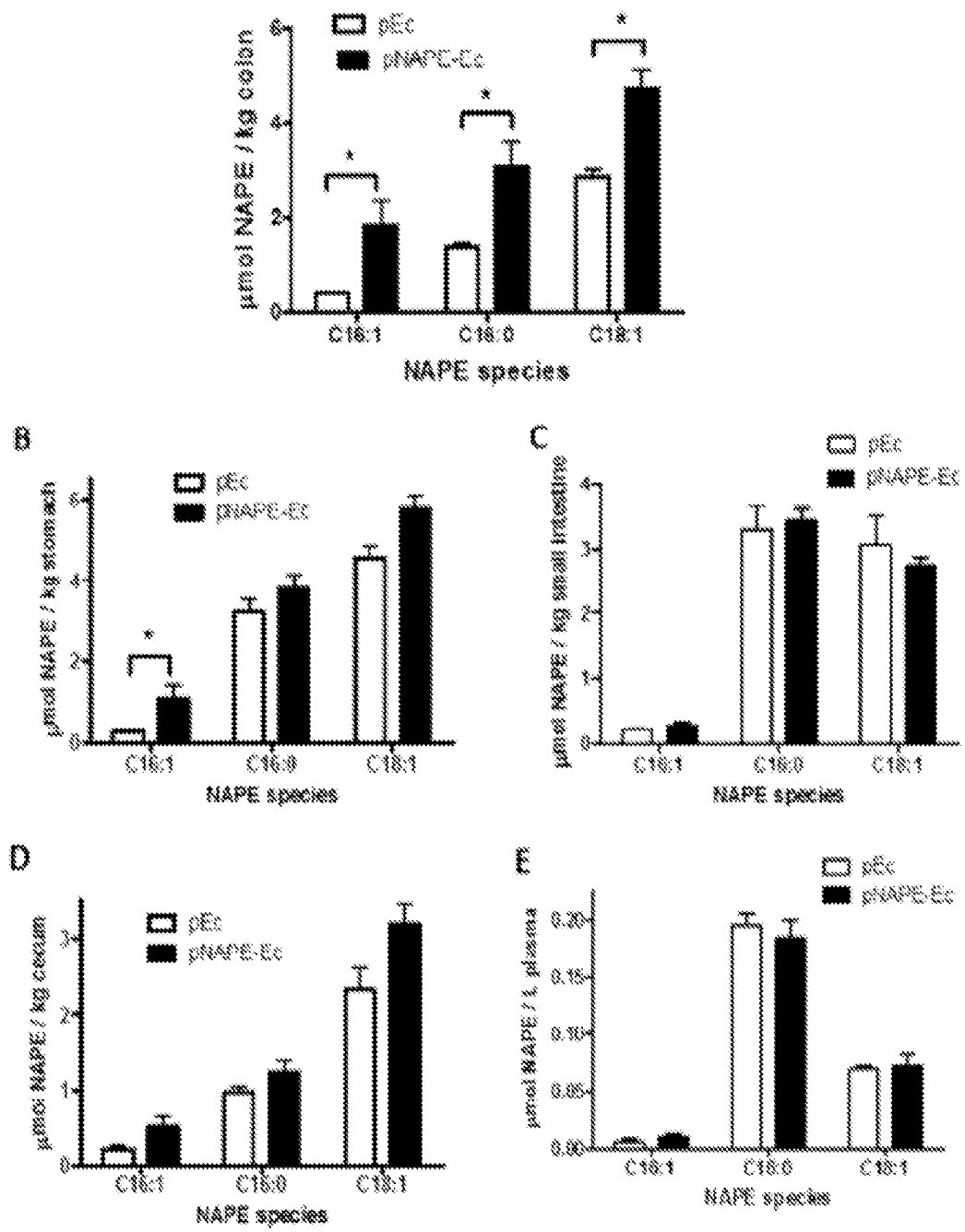
FIG. 4. NAPEs expressed by bacteria is absorbed by the colon. A. NAPE levels in colon of mice (n=5 mice per group) administered a daily bolus of $10^{11}$ cfu for seven days of either pEc bacteria or pNAPE-Ec bacteria by oral gavage. Four hour after final gavage, mice were euthanized, the GI tract harvested and flushed with phosphate buffered saline solution to remove intraluminal content. NAPE levels were measured by EC/MS/MS after methylamine hydrolysis. *p<0.05 Student's t-test. All results are mean±SEM. NAPE levels were also measured in stomach (B), small intestine (C), cecum (D), and plasma (E) of these same mice. That changes in NAPE levels were primarily in the colon is consistent with what is known about *E. coli* colonization of the intestinal tract.

The availability of bacterial membrane lipids for absorption by intestinal cells is unknown. To test whether bacterially synthesized NAPE was absorbed by the intestine, pNAPE-Ec or pEc bacteria was administered by oral gavage to C57BL6 mice. Administration of 1011 pNAPE-Ec bacteria once a day for seven consecutive days resulted in an approximately two-fold increase in NAPE levels in the colon (FIG. 4). NAPE levels were not as markedly increased in other gastrointestinal tissues besides the colon such as stomach, small intestine, and cecum, nor were they increased in plasma.

Figure 5:
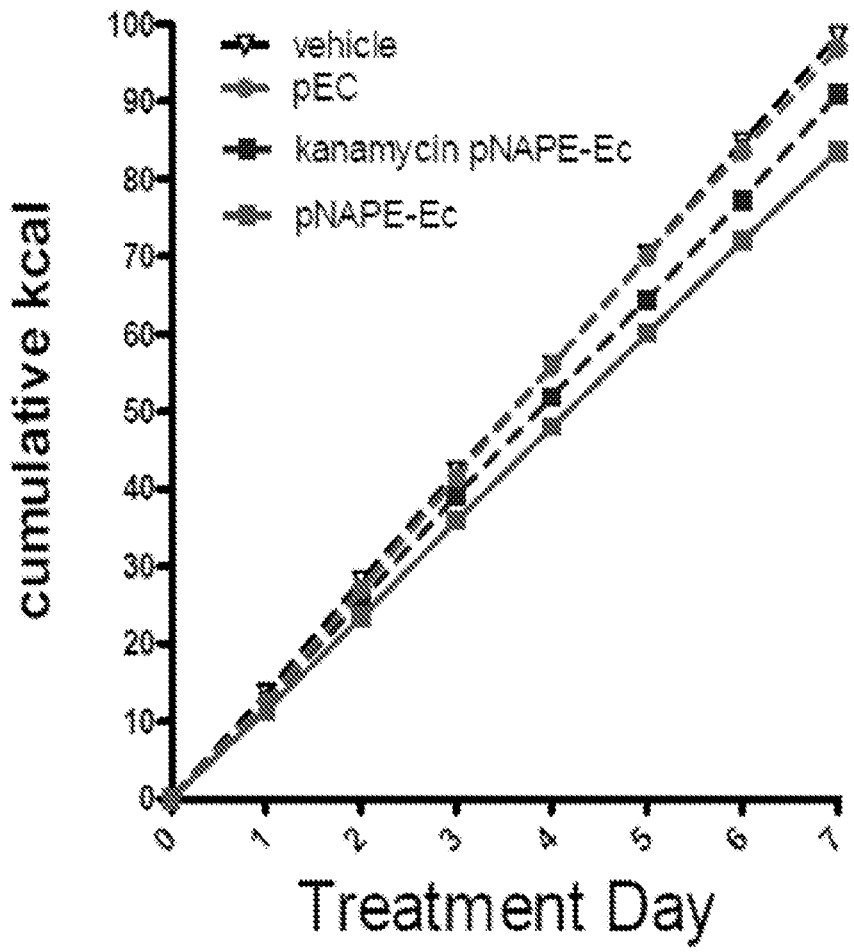
FIG. 5. Administration of living bacteria secreting NAPE reduces cumulative food intake in lean mice. Groups of lean C57BL6 mice (n=5 mice per group) were administered a daily bolus of $10^{11}$ cfu of pEc, pNAPE-Ec bacteria, or kanamycin-killed pNAPE-Ec bacteria by oral gavage for seven days. All mice received chow diets. Vehicle was LB broth without bacteria. 2-way RM ANOVA p<0.0001 for interaction of time and treatment. pNAPE-Ec differed from vehicle by Bonferroni post-hoc multiple comparison at day 6 and 7 (p<0.01).

To determine if the observed increases in colonic NAPE levels were sufficient to alter food intake, a daily bolus of 1011 cfu pNAPE-Ec or pEc bacteria was again administered by gavage to lean C57BL6 mice for seven days. Additional groups of mice were administered either vehicle only or pNAPE-Ec bacteria that had been killed by treatment with kanamycin prior to gavage. Cumulative food intake did not differ in mice receiving pEc compared to vehicle, but was reduced 15% in mice receiving living pNAPE-Ec (FIG. 5). pNAPE-Ec pretreated with kanamycin prior to gavage did not reduce food intake to the same extent as untreated pNAPE-Ec, indicating that viable bacteria expressing NAPE are needed for maximum effectiveness.

Figure 6:
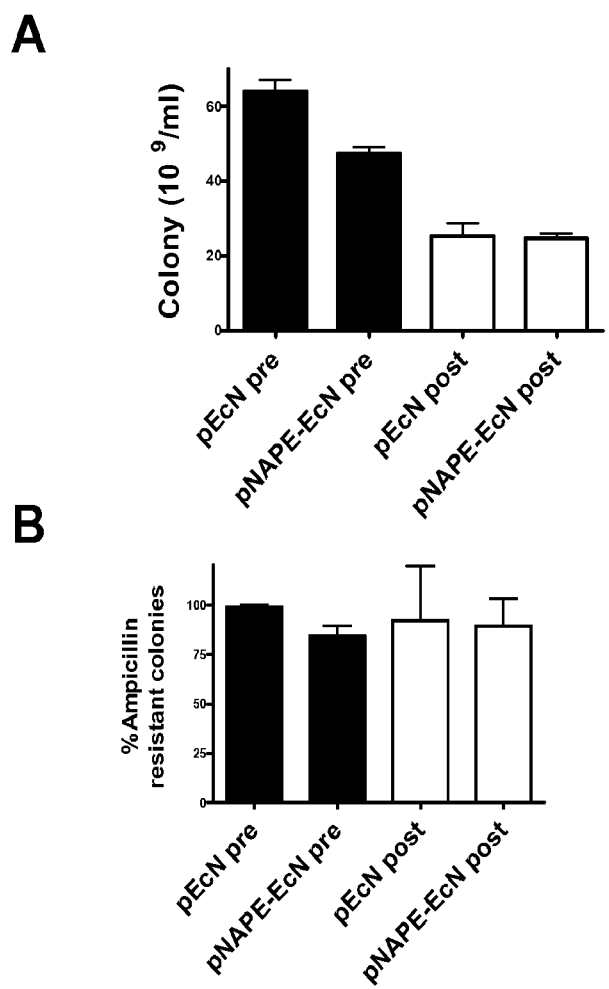
FIG. 6. Viability and retention of NAPE expression plasmid during incubation of pNAPE-EcN in drinking water for 48 h. A. The number of viable bacteria present in drinking water supplemented with $5\times10^9$ cfu/ml pEcN or pNAPE-EcN prior to (pre) and following (post) 48 incubation at room temperature. (n=3 per group). B. Percent of viable colonies that maintained subsequent ampicillin resistance (i.e. NAPE expression plasmid) despite incubation without selection for 48 h.
Figure 7:
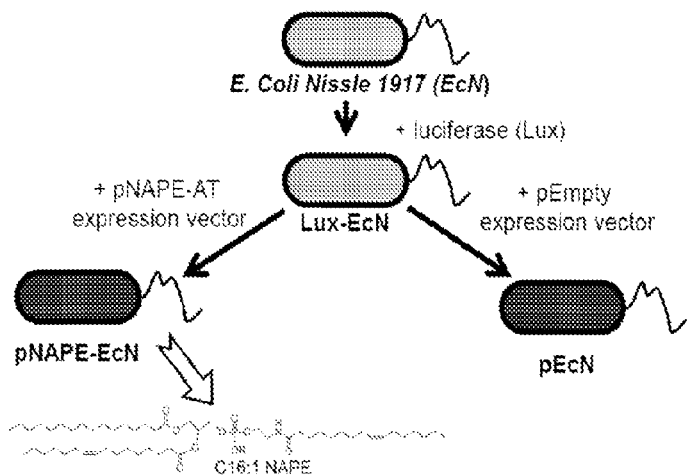
FIG. 7. Study design. A. Construction of therapeutically modified bacteria. The probiotic bacterium *E. coli* Nissle 1917 (EcN) was modified to secrete N-acyl-phosphatidylethanolamines (NAPEs) by transformation with an expression plasmid for the *A. thaliana* NAPE acyltransferase (At1g78690p). To enable tracking of EcN by bioluminescence, the *P. luminescens* luciferase operon was inserted into the RecA gene of EcN prior to transformation with either empty expression plasmid (pEcN) or the NAPE acyltransferase expression plasmid (pNAPE-EcN). B. Animal studies. Male C57BL6 mice (n=10 mice per group) were given ampicillin for the 7 days prior to starting treatment with bacteria. At start of treatment, all mice began a high fat diet. Mice were treated using drinking water supplemented with $5\times10^9$ cfu/ml pNAPE-EcN, $5\times10^9$ cfu/ml pEcN, 0.125% gelatin (vehicle), or no treatment (water). Food intake and body weight were measured three times per week and body fat composition and kaolin intake were measured once a week. An oral glucose tolerance test (OGTT) was performed after the last treatment day. After cessation of bacterial treatment, food intake and body parameters were followed for another 4 weeks.
Figure 7:
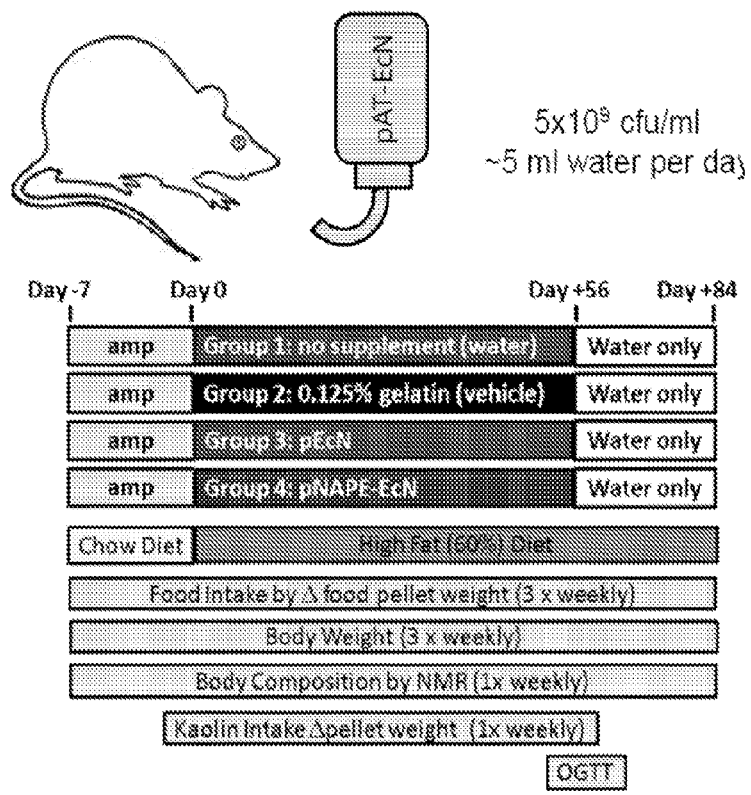
Figure 8:
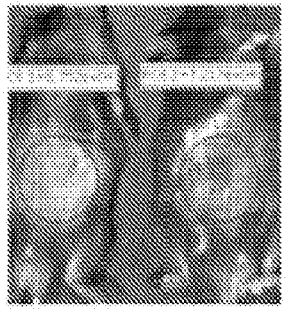
FIG. 8. pNAPE-EcN supplemented in drinking water accumulates in the gut. Mice were given either standard drinking water (water only) or water supplemented with $5\times10^9$ cfu of pNAPE-EcN (which are bioluminescent due to insertion of luciferase operon) for four days. The underbellies of the mice were shaved to reduce light absorbance during emission from the gut. Emitted luminescence was measured by IVIS imaging system. Luminescent intensity is shown as false color overlaid on black and white image of mice, with the quantified intensity within the region of interest (ROI) shown above each animal.
Figure 8:
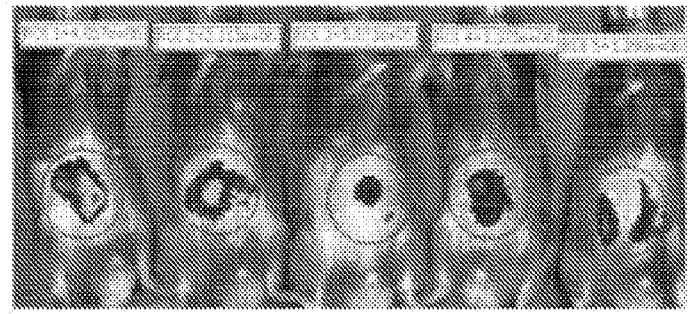

It was then tested whether remodeling gut microbiota to include bacteria expressing NAPEs would protect against the development of obesity, insulin resistance, and liver steatosis that occurs in C57BL6 mice fed a high fat diet (60% calories from fat) ad libitum. For these experiments, pNAPE-EcN was used rather than pNAPE-Ec, in order to increase the likelihood of colonization. pEcN were used as controls. These bacteria were also administered in the mice's drinking water at 5×109 cfu bacteria/ml with 0.125% gelatin added to the water to keep the bacteria suspended and viable for at least 48 h (FIG. 6). Bacteria were administered for a total of 8 weeks (FIG. 7). Supplementation of drinking water with pNAPE-EcN/ml resulted in bioluminescence that could be readily detected in the intestinal tract (FIG. 8). Food intake, gain in body weight, and body composition were monitored at regular intervals. Consumption of kaolin (pica), a measure of gastrointestinal distress in rodents[27], was also monitored to assess whether bacterial administration had an adverse effect on the mice. At the end of the bacterial treatment period, an oral glucose tolerance test was performed to assess insulin resistance. Mice were continued on the high-fat diet for an additional 4 weeks to determine the persistence of the altered gut microbiota and the resulting changes in food intake and obesity.

Figure 9:
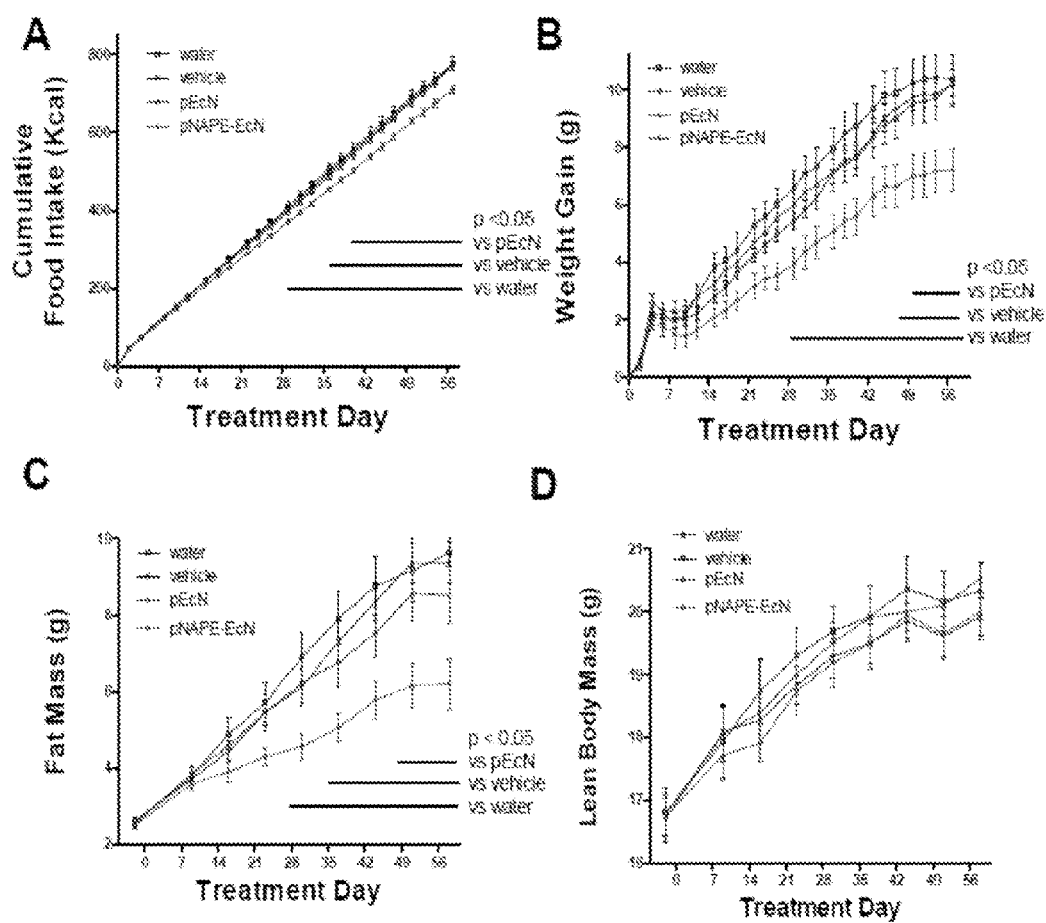
FIG. 9. Mice treated with *E. coli* Nissle 1917 secreting NAPE (pNAPE-EcN) have reduced food intake, body weight gain, and adiposity when fed a high-rat diet. A. Effect of treatments on cumulative food intake. 2-wayRM-ANOVA treatment p=0.0035, time p<0.0001. Solid bars indicate time points with significant differences between pNAPE-EcN and other groups (p<0.05 Bonferroni's post test). B. Effect of treatments on gain in body weight (2wayRM-ANOVA, treatment p=0.0073, time p<0.0001.) C. Effect of treatment on fat mass (2wayRM-ANOVA, treatment p=0.0127, time p<0.0001.) D. Effect of treatment of lean body mass. (2wayRM-ANOVA, p=0.8113 treatment, time p<0.001.) All values are mean±s.e.m.

During the 8 week treatment period, the cumulative food intake of mice treated with pNAPE-EcN was markedly lower than those treated with standard water, vehicle, or pEcN (FIG. 9A). pNAPE-EcN treated mice also gained less body weight (FIG. 9B). These differences in body weight were the result of significantly reduced accumulation of fat mass by the pNAPE-EcN treated mice (FIG. 9C). Consistent with this reduced adiposity, pNAPE-EcN had lower plasma support the conclusion that increased satiety induced by NAPE caused the reduced food intake and concomitant reduced adiposity that resulted from pNAPE-EcN treatment.

TABLE 3

Effects of NAPE secreting bacteria on metabolic biomarkers during 8 week treatment and 4 week follow-up period.

|  | water only (n = 10) | Vehicle (n = 10) | pEcN (n = 10) | pNAPE-EcN (n = 10) | 1 way-ANOVA |
|---|---|---|---|---|---|
| Fasting Plasma Week 8 | | | | | |
| Glucose (mg dL$^{-1}$) | 124 ± 17 | 114 ± 13 | 117 ± 24 | 110 ± 11 | p = 0.356 |
| Leptin (ng mL$^{-1}$) | 40.4 ± 13.8 | 40.6 ± 12.3 | 31.0 ± 13.7 | 15.8 ± 5.8 | P < 0.0001 |
| Insulin (ng mL$^{-1}$) | 1.41 ± 0.33 | 1.23 ± 0.47 | 0.70 ± 0.38 | 0.42 ± 0.16 | P < 0.0001 |
| Oral Glucose Tolerance Test Week 8 (AUC mg/dl*h) | 573 ± 67 | 547 ± 62 | 540 ± 76 | 470 ± 53 | p = 0.008 |
| Body Weight (g) | | | | | |
| Week 0 | 23.3 ± 1.8 | 23.1 ± 1.6 | 23.1 ± 1.6 | 23.2 ± 1.3 | p = 0.994 |
| Week 8 | 33.6 ± 3.7 | 33.4 ± 2.6 | 33.3 ± 2.9 | 30.4 ± 2.7 | p = 0.070 |
| Week 12 | 36.5 ± 4.8 | 36.6 ± 3.5 | 35.7 ± 3.8 | 32.1 ± 3.4 | p = 0.043 |
| % Body Fat (g/g) | | | | | |
| Week 0 | 11.4 ± 1.6 | 11.5 ± 1.6 | 11.2 ± 1.3 | 11.0 ± 1.3 | p = 0.876 |
| Week 8 | 27.9 ± 4.8 | 28.0 ± 2.9 | 25.2 ± 5.3 | 20.0 ± 5.5 | p = 0.002 |
| Week 12 | 30.9 ± 6.1 | 31.5 ± 3.3 | 27.4 ± 6.5 | 22.3 ± 5.5 | p = 0.002 |
| Cumulative Calories Consumed (kcal) | | | | | |
| Week 0 to 8 | 778 ± 52 | 773 ± 32 | 771 ± 36 | 711 ± 33 | p = 0.012 |
| Week 9 to 12 | 381 ± 35 | 388 ± 20 | 395 ± 21 | 355 ± 26 | p = 0.010 |
| Liver Triglycerides Week 12 (μg/mg) | 36.5 ± 9.2 | 41.1 ± 26.1 | 27.2 ± 9.5 | 16.1 ± 9.6 | p = 0.006 |

TABLE 4

Effect of pNAPE-EcN administration on muscle strength, speed, and coordination.

|  | Water | Vehicle | pEcN | pNAPE-EcN | ANOVA |
|---|---|---|---|---|---|
| Inverted screen latency to fall (secs)† | 50.7 ± 18.8 | 50.6 ± 13.3 | 57.6 ± 7.6 | 53.0 ± 14.82 | 0.6637 |
| Wire hang latency to fall (secs)† | 32.2 ± 21.2 | 43.7 ± 18.9 | 52.5 ± 12.8 | 53.8 ± 12.7 | 0.0249 |
| Pole descent latency (secs) | 15.7 ± 5.7 | 12.6 ± 2.1 | 17.0 ± 6.7 | 12.8 ± 5.7 | 0.1920 |

Figure 10:
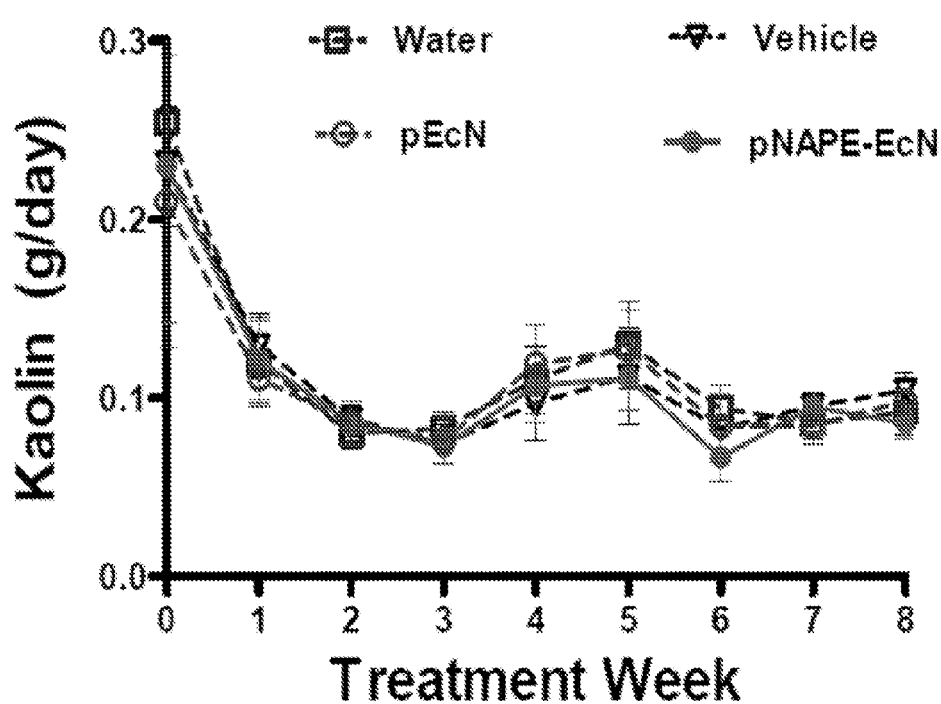
FIG. 10. Supplementation of drinking water with bacteria did not induce gastrointestinal distress. Distress was monitored by consumption of kaolin clay pellets (pica), with pre-weighed pellets added to the cages and change in pellet weight measured once a week and then averaged per day. Results are shown as mean±s.e.m. (n=10 mice per group). There was no significant difference between groups.
Figure 11:
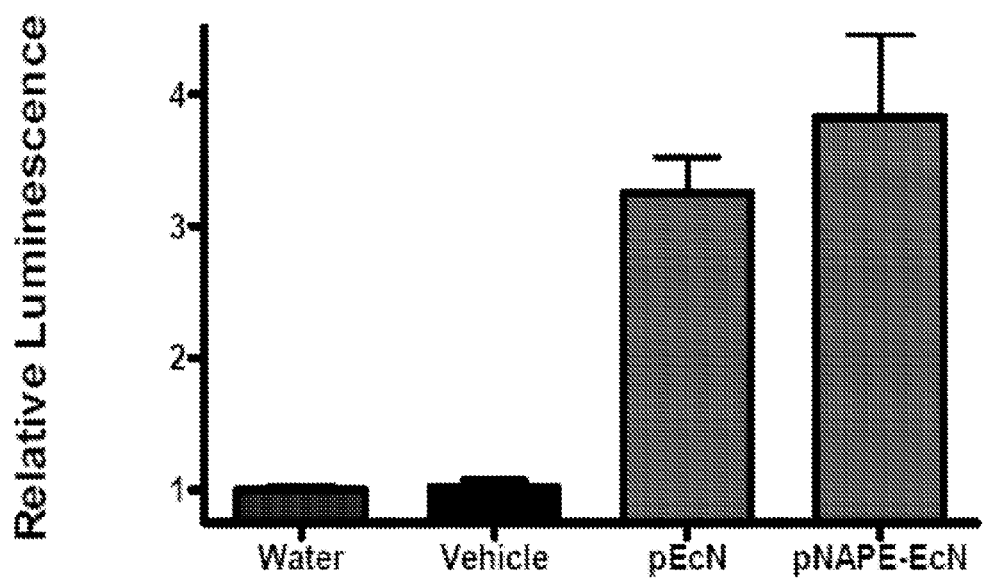
FIG. 11. Secretion of NAPE does not cause overgrowth of EcN. Intestinal levels of pEcN and pNAPE-EcN were measured by in vivo imaging (n=10 per group). Bioluminescence levels were not significantly different between pEcN and pNAPE-EcN, indicating that differences in food intake and adiposity are not the result of increased bacterial load.
Figure 12:
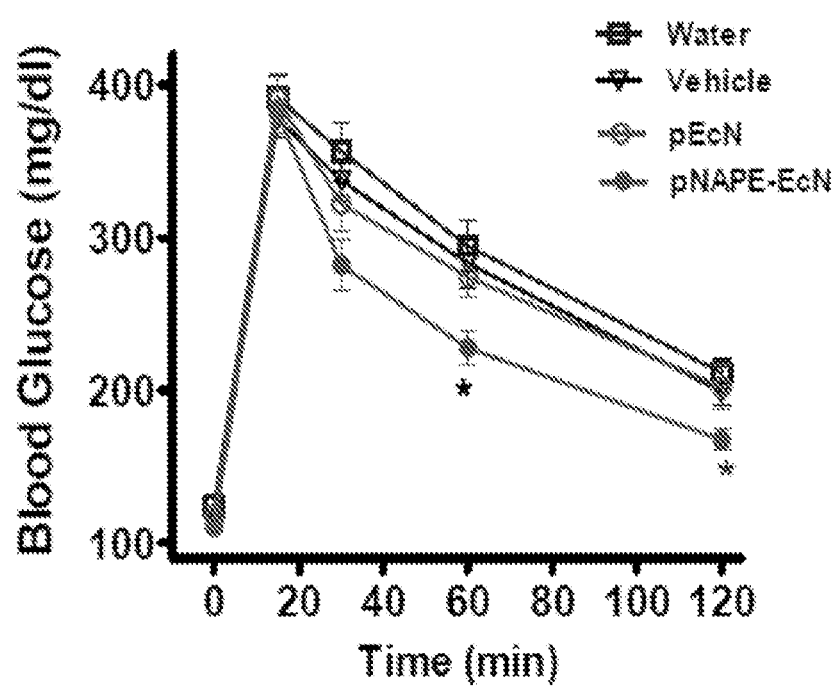
FIG. 12. Treatment with pNAPE-EcN for 8 weeks improves glucose tolerance. Response of blood glucose to oral bolus of glucose (2 g/kg body weight) was measured of 120 min. Results shown as mean±SEM (n=10 mice per group). *p<0.05 1wayANOVA for time point. All values are mean±s.e.m.
Figure 13:
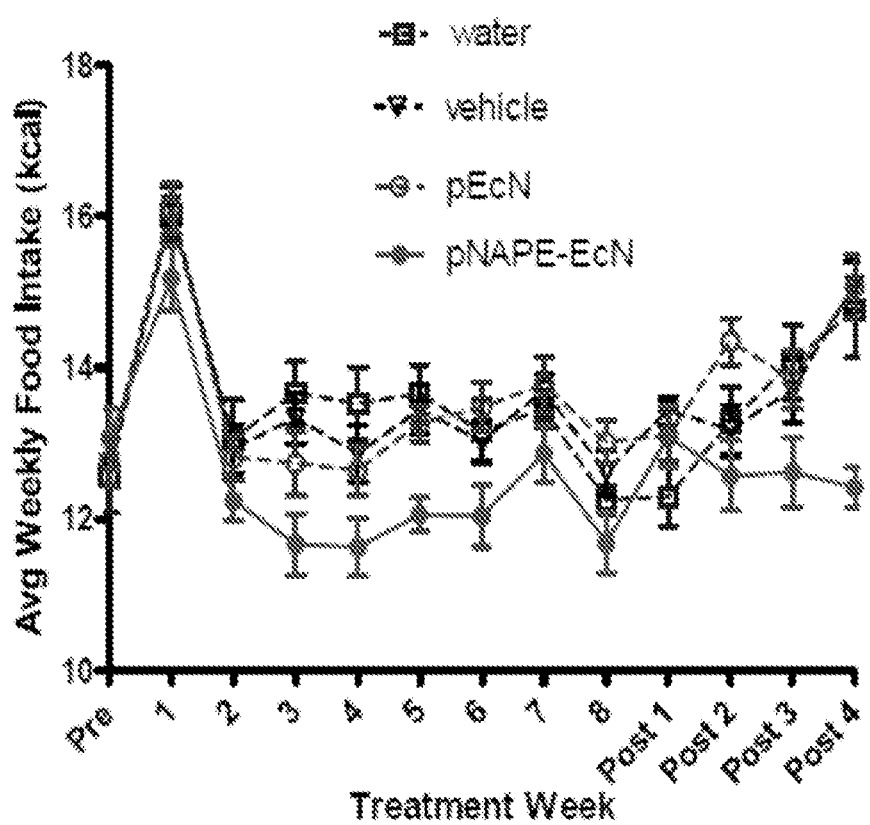
FIG. 13. Beneficial effects of pNAPE-EcN on food intake persist for at least 4 weeks after cessation of bacterial administration. Food intake was measured by change in food pellet weight three times per week, converted to kcal, then averaged for the week.
Figure 14:
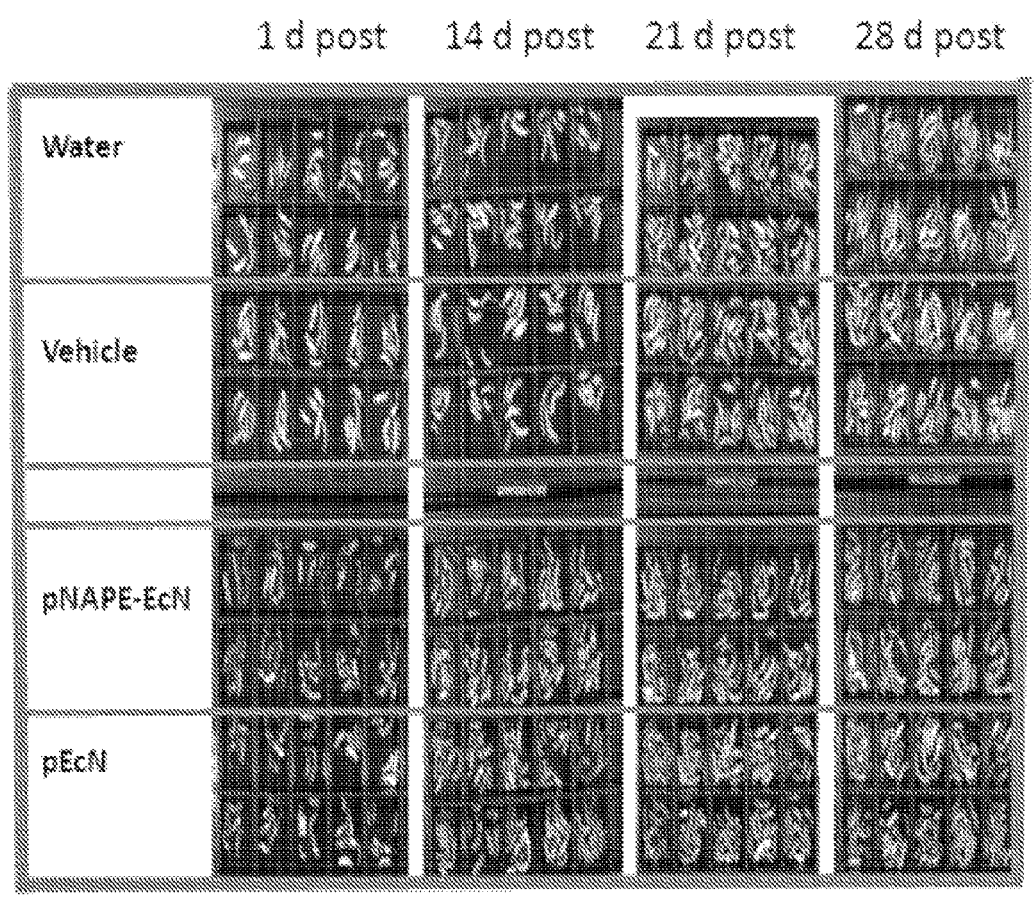
FIG. 14. Bioluminescent bacteria continue to be excreted in feces for at least 4 weeks after cessation of bacterial administration. Feces from each mouse cage (n=10 mice per group) were collected 1 day, 14 days, 21 days, and 28 days post-treatment and placed in 24-well plates (1 well per mouse). Luminescence of all feces for an individual collection day were measured simultaneously using an IVIS instrument and images for separate collection days have been placed side by side above. Intensity is displayed using false-color.

†Maximum latency to fall allowed was 60 secs.

leptin levels than the other groups (Table 3). In contrast to the striking differences in adiposity, there were no significant differences in lean body mass between the groups (FIG. 9D). Importantly, no evidence was found that the changes in body weight and adiposity were the result of an adverse effect of treatment with pNAPE-EcN on health. For instance, there was no difference between treatment groups in the consumption of kaolin (FIG. 10), so bacterial administration did not produce gastrointestinal distress. Nor did bacterial overgrowth appear to be the cause of reduced food intake and adiposity in pNAPE-EcN treated mice, as levels of EcN retained in the intestinal tract did not significantly differ between pNAPE-EcN and pEcN treated mice (FIG. 11). Furthermore, mice given pNAPE-EcN had lower fasting insulin levels (Table 3) and significantly improved glucose tolerance compared to the other groups (FIG. 12), which is consistent with improved insulin sensitivity and strongly suggests that the reduced food intake was not due to endotoxemia as this significantly impairs insulin sensitivity[6,7]. Finally, scores on simple tests of muscle strength, coordination, and speed either did not differ or were improved with pNAPE-EcN treatment (Table 4). These findings strongly The larger goal was to achieve long-term remodeling of the gut microbiota with these NAPE secreting bacteria in order to endow their host with long-term resistance to obesity. It was therefore investigated whether the beneficial effects of these bacteria would persist after stopping their administration. Food intake during the follow-up period (experimental weeks 9 to 12) remained significantly lower in mice initially treated with pNAPE-EcN than for the other groups (Table 3) and their average weekly food intake for this period was similar to that of the treatment period (FIG. 13). Most importantly, the lower body weight and fat mass observed for pNAPE-EcN treated mice during the treatment period was maintained during the four week follow-up period (Table 3), consistent with the goal of conferring long-term protection against obesity induced by diet. Mice initially treated with either pNAPE-EcN or pEcN excreted luminescent bacteria in their feces for at least four weeks after the cessation of bacterial administration (FIG. 14), consistent with persistence of pNAPE-EcN in the gut.

The results demonstrate the feasibility of remodeling gut microbiota to secrete small molecules beneficial to their host and to thereby prevent or treat chronic conditions such as obesity that increase morbidity and mortality. This approach might be more cost effective than chronic drug regimens and more easily complied with than intensive interventional approaches for the treatment of obesity such as self-imposed caloric restriction and exercise or bariatric surgery. This advantage stems from the persistence of the bacteria in the gut after the initial treatment period, removing the requirement for sustained actions by the affected individual. Another advantage of this approach for small molecules that are active in the gut like NAPE is that their biosynthesis near their site of action could minimize off-target exposure and reduce the amount needed for efficacy. A final possible advantage of this approach is that timing of biosynthesis could be made directly responsive to food intake by use of appropriate promoters. Such food-dependent biosynthesis would mimic physiological regulation of many metabolic responses, potentially improving efficacy. Thus the studies demonstrate both a straight-forward approach to ameliorate obesity and the feasibility of similar approaches for the treatment of other chronic conditions.

Methods

Method Summary.

*E. coli* Nissle 1917 (EcN) were rendered bioluminescent by insertion of *P. luminescens* luciferase operon into the RecA gene of EcN. These bioluminescent EcN were then transformed either with an empty expression vector (pEcN) or the same vector which had the *A. thaliana* N-acyltransferase At1g78690 inserted (pNAPE-EcN). *E. coli* C41-DE3 (Ec) transformed with At1g78690 (pNAPE-Ec) as previously described[24] were also used for initial studies. NAPE concentration was quantified by LC/MS/MS after methylamine hydrolysis[25]. The nucleotide sequence for *Arabidopsis* N-AT is set forth in SEQ ID NO: 1. The accession number for *Arabidopsis* N-AT is AEE36139.

```
                                              (SEQ ID NO: 1)
ATGGCTATGGGAAGATAATGGAATGGGCAGCAAGATCTGATCATTTGGG

AGGAATTCCAAGGAATACTGTGATAATGGCTGTTAGTGCATTTGCAAAAG

CAGTAGCAAATCTTTGCAATAAAAGCTCAGTTCACAATGCAGATACTCTT

ATGAATCTTGTCCAGTCAAGACCACCTGGTGTTCCTCTCATCACTGTTAG

TAATCACATGTCGACTTTGGATGATCCAGTAATGTGGGGGCATTTAAGG

GTCTCCTTTCCTTAGATCCAGAATTGGCTCGGTGGGTTCTTGCTGCAGAG

GATATATGTTTCAGGAACCCTATATTCTCCTACATTTTCCGCACTGGAAA

ATGTATACCTATAACTAGAGGTGGTGGAATCTACCAAGAAAACATGAATG

AAGCTCTCCAGCGATTAAAAGATGGATCTTGGCTGCATACCTTCCCAGAG

GGAAAGGTGTTTCAAGATGATGTTCCTATAAGACGACTTAAATGGGAAC

TGCAAGCCTCATCGCCCGTTCCCCAGTTACCCCAATCGTTTTGCCAATAA

TTCACCGTGGTTTTGAGGAGATGATGCCGGAGAACTACAATAATGGACGA

AGACCACTGGTACCGTTGCCGAACAAACACCTTAAAGTTGTGGTTGGTGA

ACCAATTGAGTTTGATGTTCCAATGATGGTTGAGACTGCTGTCTTGGACT

CCCGCCATGTAACCCCTCCTCTTCAAGAAGTGAAATGGCCTGTCCTCACT

TCTGCTGGCCAAGTGCTAGACGAAACTGCTCAGAGACACCTCTACATAGC

TCTGTCCGAGAAGATTCAATCCTCCTTGGAAACATTGAGACTCTTAGCCA

AGCGGTTGTGA
```

Prior to bacterial treatment, all mice were treated with 500 mg/L ampicillin in drinking water for seven days. For studies on NAPE absorption, 12 week old male C57BL/6J in were administered $10^{11}$ cfu of pEc or pNAPE-Ec (n=5 per group) by oral gastric gavage once a day for seven days. Mice were sacrificed four hours after the last gavage. For diet-induced obesity study, six week old C57BL/6J mice were distributed into four groups (n=10 mice per group) so that the mean and variation in body weight and body fat for each group was as similar as possible (Table 3). Body composition was determined by NMR. Each group was then randomly assigned one of the four treatments in their drinking water: no additives (water), 0.125% gelatin (vehicle), $5 \times 10^9$ cfu/ml pNAPE-EcN (pNAPE-EcN), or $5 \times 10^9$ cfu/ml pEcN (pEcN) and were simultaneously fed a 60% fat diet. Mice were also given access to kaolin clay pellets. Food intake, body weight, body composition, and kaolin consumption were measured at regular intervals. After 8 weeks, mice were returned to standard drinking water, fasted overnight and given an oral glucose tolerance test (2 g/kg body weight). The mice were continued on 60% fat diet for another four weeks, with feces collected once a week, and then mice were sacrificed and liver triglycerides determined.

Bacterial Strains and Preparation.

The pDEST-At1g78690 expression plasmid and transformation into *E. coli* C41-DE3 (Ec) have been previously described[24]. *E. coli* Nissle 1917 (EcN) was obtained from Metaflor, Inc and the *P. luminescens* luciferase operon cloned from the pXen5 plasmid (Xenogen) inserted into the RecA gene. For expression of At1g78690 in EcN, pQE-80L (Qiagen) was modified by removing one lac operator to enable basal expression of inserted genes without IPTG induction. This was accomplished by digesting pQE-80L with XhoI and EcoR1 and then annealing two pairs of oligos that had previously been annealed and then digested with the same enzymes. The sequences of these oligos are: pair 1. Sense: TCGTCTTCAC CTCGAGAAAT CATAAAAAAT TTATTTGCTT TGTGAGCGGA TAACAATTAT AATAGATTCA ATCACACAGA ATTCATTAAA (SEQ ID NO: 2); Antisense: TTTAATGAAT TCTGTGTGAT TGAATCTATT ATAATTGTTA TCCGCTCACA AAGCAAATAA ATTTTTTATG ATTTCTCGAG GTGAAGACGA (SEQ ID NO: 3). Pair 2. Sense: TCGTCTTCAC CTCGAGAAAT CATAAAAAAT TTATTTGCTT TCAGGAAAAT TTTTCTGTAT AATAGATTCA ATCACACAGA ATTCATTAAA (SEQ ID NO: 4); Antisense: TTTAATGAAT TCTGTGTGAT TGAATCTATT ATACAGAAAA ATTTTCCTGA AAGCAAATAA ATTTTTTATG ATTTCTCGAG GTGAAGACGA (SEQ ID NO: 5). The At1g78690 gene was obtained by high fidelity PCR using pDEST-At1g78690[24] as template and the following primers: Sense: CGCGGATCC A TGGCTATGGG GAAGATAATGG (SEQ ID NO: 6); Antisense: GAGAGAGCTC TCACAACCGC TTGGCTAAGA GTC (SEQ ID NO: 7), and subcloned in frame into pQE-80L1 digested with BamHI and SacI. Bioluminescent EcN were then transformed either with pQE-80L1 empty vector (pEcN) or pQE-80L1 with At1g78690 inserted (pNAPE-EcN). Transformed bacteria were resuspended at $3.33 \times 10^{11}$ cfu/ml in LB medium for oral gavage or at $5 \times 10^9$ cfu/ml in water containing 0.125% gelatin for supplementation studies.

To determine the viability of pNAPE-EcN after 48 h suspension in water containing 0.125% gelatin, aliquots of $5 \times 10^9$ cfu/ml stock were serially diluted to $5 \times 10^2$ cfu/ml and then replicate 50 ul aliquots streak on non-selective plates (to measure total cfu) or ampicillin plates (to identify colonies that retained the NAPE acyltransferase expression plasmid). After 48 h incubation, ~40% of bacteria remained viable (FIG. 6A). ~80% of bacteria retained the expression plasmid despite the lack of selection for 48 h, based on subsequent resistance of plated bacteria to ampicillin (FIG. 6B).

NAPE Measurement.

NAPE concentration was quantified by LC/MS/MS after methylamine hydrolysis, as previously reported[25]. Because Bulat and Garrett[26] recently reported that they failed to find evidence for significant synthesis of NAPE in *E. coli* expressing At1g76890p, the present inventors performed additional experiments to confirm the synthesis of NAPE in the engineered EcN. To determine if the analyzed methylamine hydrolyzed species did indeed arise from NAPE and not from lysoNAPE or acyl-PG, an aliquot was taken prior to methylamine hydrolysis and analyzed by limited mass scanning in negative ion mode after HPLC to separate phospholipid species. To confirm that the putative NAPE species did indeed contain N-acyl headgroups, and were not simply acyl-PG species as proposed by Bulat and Garrett, the present inventors performed base hydrolysis with 0.35 M methanolic sodium hydroxide for two hours, removed salts from the neutralized reaction mixture via C18 solid phase extraction, and then analyzed the products on LC/MS in full scanning mode using the same HPLC gradient as for the methylamine hydrolyzed products.

Animal Studies.

All animal experiments were performed according to protocols approved by the Institutional Animal Care and Use Committee at Vanderbilt University. Four or 12 weeks old male C57BL/6J mice were purchased from the Jackson Laboratory.

For preliminary studies to determine NAPE absorption after gavage and the effect on food intake, 12 week old male C57BL/6J mice were treated with 500 mg/L ampicillin in drinking water for seven days and then administered $10^{11}$ cfu of pEc or pNAPE-Ec by oral gastric gavage using a ballpoint metal syringe. For studies on NAPE absorption and food intake, mice were given a single daily dose of bacteria for seven days. For studies examining the effect on food intake, mice were given a single daily dose of $10^{11}$ cfu bacteria for seven days. Daily food intake was measured by adding pre-weighed food pellets to each cage and then re-weighing these pellets after 24 h. Four hours after the last gavage, mice were sacrificed and blood and tissue collected.

All bioluminescence imaging (BLI) was performed using an IVIS 200 CCD camera (Xenogen/Caliper). Equal areas for each regions of interest (ROI) were centered over the bioluminescent region. Photon counting measurements summed bioluminescent intensity for all pixels within the ROI over the integration time.

For diet-induced obesity study, forty male C57BL/6J mice were obtained at approximately four weeks of age and initially fed a standard chow diet. After one week of adaptation to the animal facility (experimental day −7), the mice were separated into individual cages and were treated with 500 mg/L ampicillin in drinking water for seven days. During this time, food intake, body weight, and body composition was determined for each mouse and then the mice were divided into four groups (10 mice each) so that the mean and variation in body weight and body fat for each group was as similar as possible (Table 3). Each group was then randomly assigned to one of the four treatment groups. On experimental day 0, ampicillin treatment was stopped, mice began receiving their assigned treatment for 8 weeks, and began the high fat diet (TestDiet® D12492, Richmond, Ind., containing 60% fat by kcal) which they received for the remainder of the study. The four treatment groups were: standard drinking water with no additives (water), with 0.125% gelatin (vehicle), with 0.125% gelatin and 5×10 cfu/ml pNAPE-EcN (pNAPE-EcN), or with 0.125% gelatin and 5×10$^9$ cfu/ml pEcN (pEcN). Additionally, all mice were given pre-weighed kaolin pellets (Research Diets, New Brunswick, N.J.) and the change in kaolin pellet weight measured once a week as an indicator of intestinal distress. On the final day of the study (Day 87), mice were euthanized and blood and tissue collected.

For body composition, mice were scanned by magnetic resonance imaging (MRI) using a Bruker Minispec MQ10 NMR Analyzer to determine fat mass, lean mass, and free fluid. For glucose tolerance testing, mice were fasted overnight, weighed, and then given a bolus of glucose (2 g glucose/kg body weight) by oral gastric gavage. Blood glucose was measured at 0, 15, 30, 60, and 120 min after gavage using the Accu-Chek Diabetes monitoring kit (Roche).

Example 2

Additional studies were performed with bacteria that co-express N-acyltransferase (N-AT) and N-acyl phosphatidylethanolamine phospholipase D (NAPE-PLD). Mice received either bacteria expressing *Arabidopsis* N-AT (pNAPE-EcN) or bacteria that co-express both N-AT and NAPE-PLD (pNAE-EcN).

As described above, *E. coli*, Nissle 1917 (EcN) were transformed with an N-AT that catalyzes the synthesis of NAPES (pNAPE-EcN). *E. coli*, Nissle 1917 (EcN) were also transformed with both *Arabidopsis* N-AT and an NAPE-PLD in order to catalyze the biosynthesis of N-acylethanolamine (NAE) from NAPE (pNAE-EcN). The nucleotide sequence for *Arabidopsis* N-AT is set forth in SEQ ID NO: 1. The accession number for *Arabidopsis* N-AT is AEE36139. The nucleotide sequence for NAPE-PLD is set forth in SEQ ID NO: 8. The accession number for mouse NAPE-PLD is NM 178728.

```
                                              (SEQ ID NO: 8)
ATGGATGAGTATGAGGACAGCCAGTCTCTCCAGCGCCAAGCTATCAGTATCC

AAAAGAAACACTGAGAAAGCGCCAGAATTCAGTGCAGAATTCAGGAGGAA

GTGTGTCTTCTAGGTTCTCCAGGAAAAGCTTCAAGCTGGATTACAGACTA

GAGGAGGACGTAACTAAATCAAAGAAAGGAAAAGACGGGAGATTTGTTAA

CCCATGGCCAACATGGAAAAACATCTCCATCCCGAATGTGCTCAGATGGC

TGATAATGGAGAAGAATCACAGCGGCGTTCCAGGTTCCAAAGAGGAACTT

GACAAAGAGCTCCCGGTGCTTAAGCCATATTTTGTCAGTGACCCTGAAGA

CGCTGGAGTGAGAGAGGCTGGCTTACGAGTCACGTGGCTGGGACATGCGA

CGCTGATGGTGGAAATGGACGAGCTCATCTTCCTCACGGACCCCATGTTC

AGCTCCCGTGCCTCTCCCTCGCAGTACATGGGTCCGAAGCGGTTTCGCCG

CCCGCCGTGTACAATAAGCGAACTCCCCACGATAGATGCTGTCCTCATCA

GTCACAACCACTACGACCACCTAGACTACGGCTCGGTCCTGGCGTTGAAC

GAGCGGTTCGGCAGCGAGCTGCGGTGGTTTGTGCCCTTGGGCCTTCTTGA

CTGGATGCAGAAATGTGGCTGCGAGAACGTGATTGAGCTGGACTGGTGGG

AGGAGAACTGCGTCCCTGGCCACGACAAGGTCACCTTCGTCTTCACGCCT
```

-continued

```
TCCCAGCACTGGTGCAAAAGGACCCTCCTGGACGACAACAAGGTTCTCTG

GGGCAGCTGGTCCGTGCTAGGGCCTTGGAGTCGATTCTTCTTTGCTGGGG

ATACTGGCTACTGCCCCGCTTTTGAAGAGATTGGAAAAAGGTTTGGTCCT

TTTGACCTTGCGGCCATTCCCATCGGAGCTTATGAACCAAGGTGGTTTAT

GAAATACCAGCATGCAGACCCAGAAGATGCTGTAAGGATTCAGATTGACC

TTCAAACAAAGAGATCTGTGGCGATTCACTGGGGGACGTTTGCCTTAGCT

AATGAGCATTACCTAGAGCCGCCAGTGAAACTGAATGAAGCTCTAGAGAG

ATACGGACTTTCTTGTGAGGATTTCTTCATACTGAAGCATGGAGAGTCGA

GATACTTGAATACCGATGATAGAGCTTTTGAAGAAACATGA.
```

The primers used for amplification of NAPE-PLD were as follows: Sense primer: CGC GGATCC ATG GAT GAG TAT GAG GAC AGC CAG (SEQ ID NO: 9); and Antisense primer: GAGA GATATC TCATGTTTCTTCAAAAGCTC-TATCATCGG (SEQ ID NO: 10)

Figure 15:
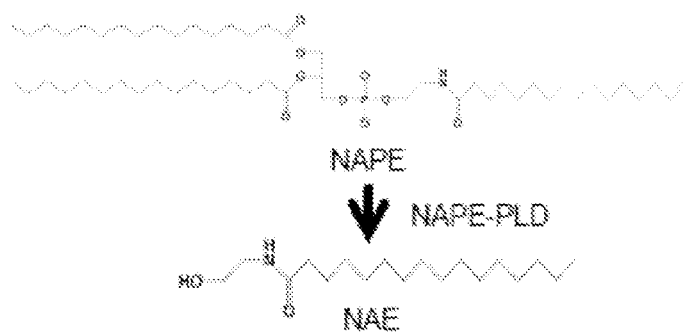
FIG. 15. Transformation of EcN to co-express both N-AT and NAPE-PLD increases levels of NAEs in EcN. NAEs are the principal species that have been shown to reduce food intake. A. Schematic of NAPE-PLD catalyzing the release of NAE from NAPE. B. Levels of individual NAPEs and NAEs in transformed EcN to express N-AT (pNAPE-EcN) and both N-AT and NAPE-PLD (pNAE-EcN).
Figure 15:
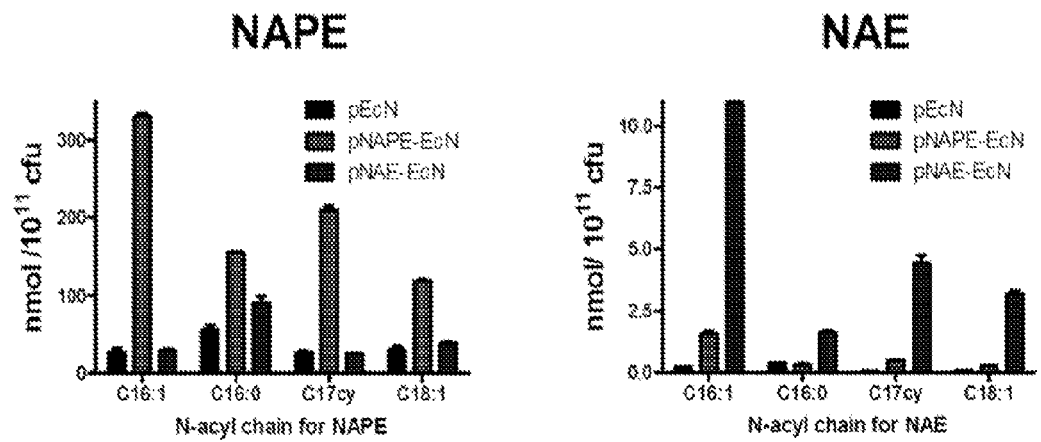

With reference to FIG. 15, transformation of EcN to express both N-AT and NAPE-PLD increases levels of NAEs in EcN. NAEs are the principal species that have been shown to reduce food intake.

Figure 16:
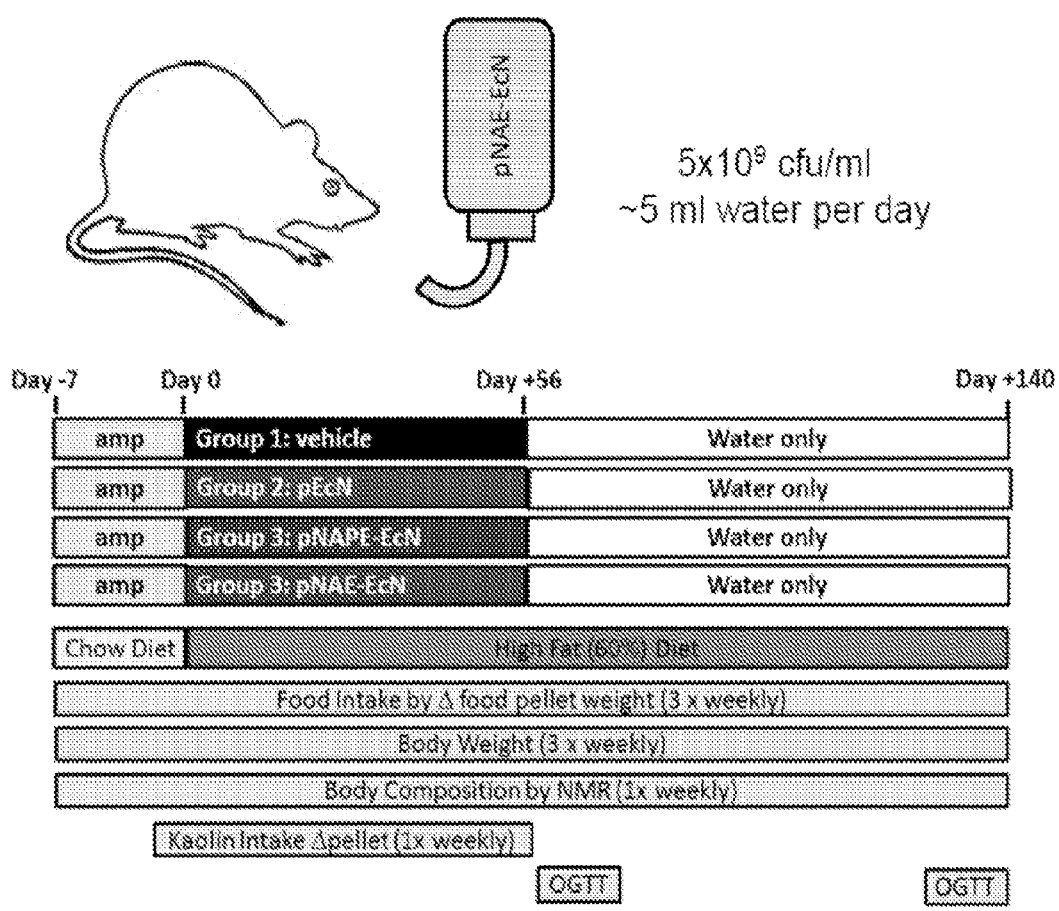
FIG. 16. Animal studies. Mice were given ampicillin for the 7 days prior to starting treatment with bacteria. At start of treatment, all mice began a high fat diet. Mice were treated using drinking water supplemented with $5 \times 10^9$ cfu/ml pNAE-EcN, $5 \times 10^9$ cfu/ml pNAPE-EcN, $5 \times 10^9$ cfu/ml pEcN, or 0.125% gelatin (vehicle) Food intake and body weight were measured three times per week and body fat composition and kaolin intake were measured once a week. An intraperitoneal glucose tolerance test (GTT) was performed after the last treatment day and again at the end of the study. After cessation of bacterial treatment, food intake and body parameters were followed for another 12 weeks.
Figure 17A:
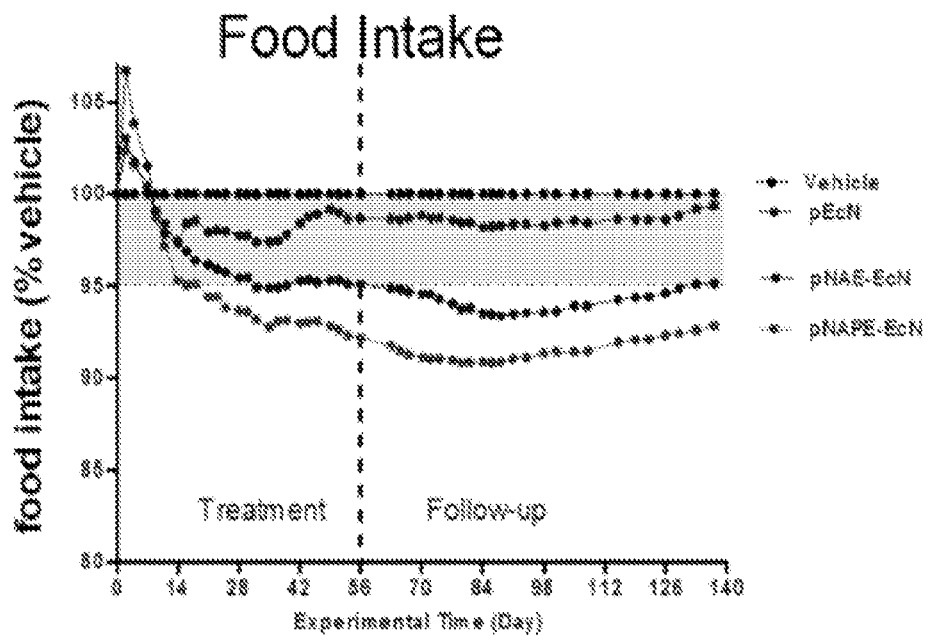
FIG. 17. Mice treated with *E. coli* Nissle 1917 secreting NAPE (pNAPE-EcN) and treated with *E. coli* Nissle 1917 secreting NAEs (pNAE-EcN) have reduced food intake (A), body weight (B), and adiposity (C) when fed a high-fat diet. An effect is seen for several weeks following cessation of treatment.
Figure 17B:
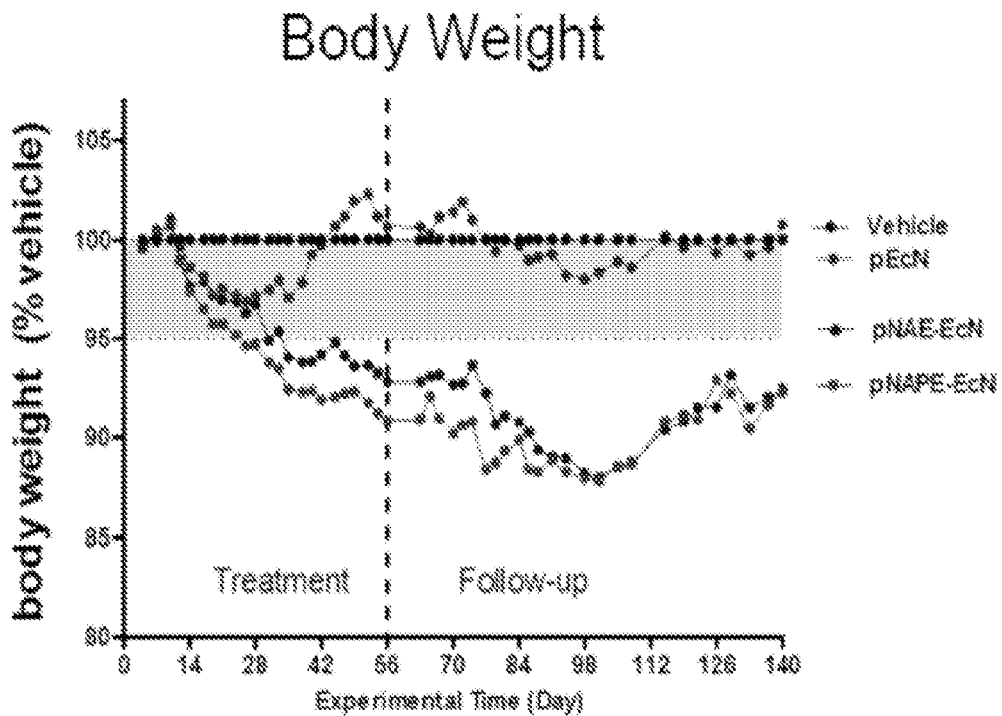
Figure 17C:
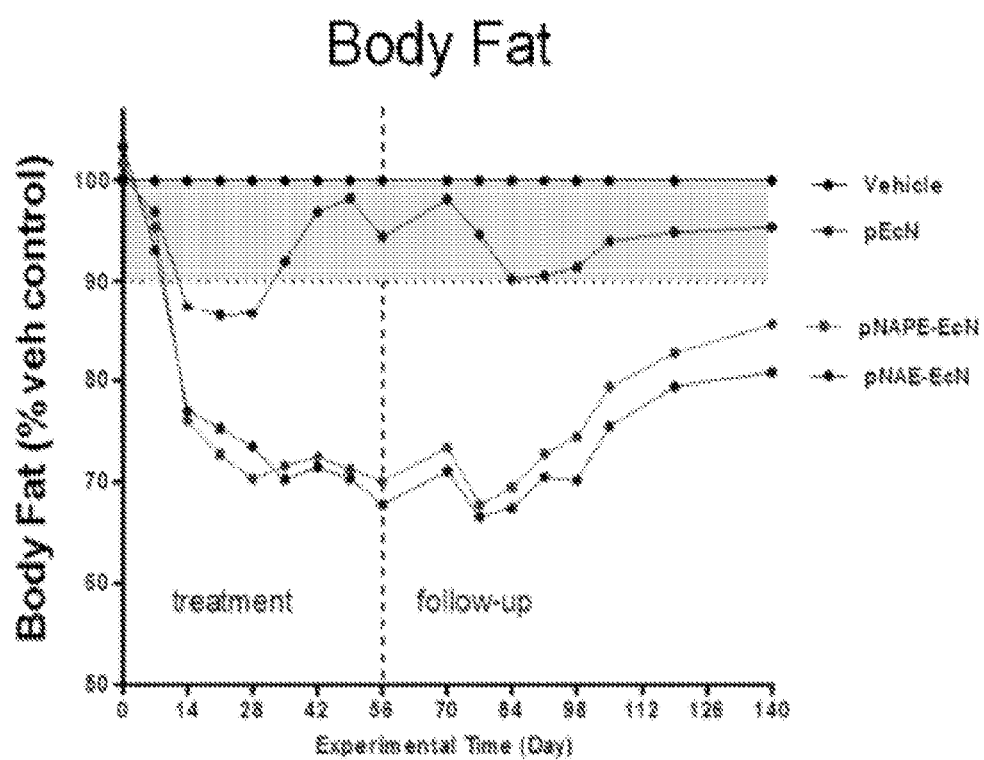

With reference to FIG. 16, mice were given ampicillin for the 7 days prior to starting treatment with bacteria. At start of treatment, all mice began a high fat diet. Mice were treated using drinking water supplemented with $5 \times 10^9$ cfu/ml pNAE-EcN, $5 \times 10^9$ cfu/ml pNAPE-EcN, $5 \times 10^9$ cfu/ml pEcN, or 0.125% gelatin (vehicle). Food intake and body weight were measured three times per week and body fat composition and kaolin intake were measured once a week. An intraperitoneal (i.p.) glucose tolerance test (GTT) was performed after the last treatment day and again at the end of the study. After cessation of bacterial treatment, food intake and body parameters were followed for another 12 weeks. As shown in FIG. 17. Mice treated with E. coli Nissle 1917 secreting NAPE (pNAPE-EcN) and treated with E. coli Nissle 1917 secreting NAE (pNAE-EcN) line reduced food intake, body weight, and adiposity when fed a high-fat diet. An effect is seen for several weeks following cessation of treatment.

Example 3

Figure 18:
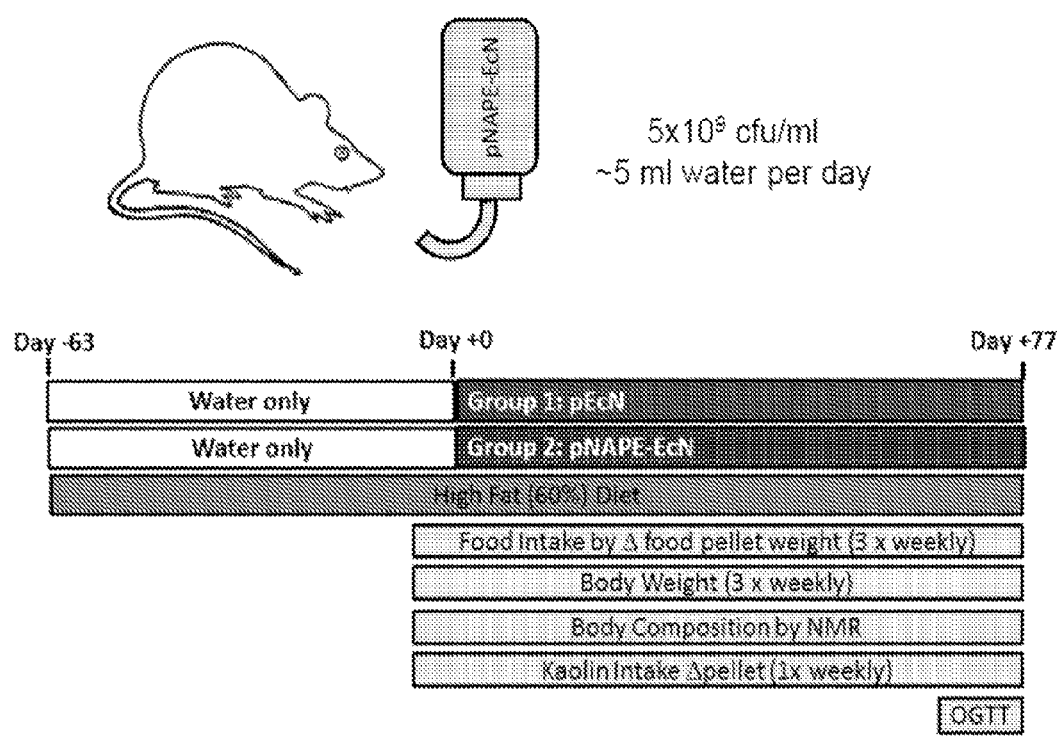
FIG. 18. Animal studies. Mice were given a high fat diet for 9 weeks prior to starting treatment with bacteria. The high fat diet continued at the start of and during treatment, which was continued for 11 weeks. Mice were treated using drinking water supplemented with $5 \times 10^9$ cfu/ml pNAPE-EcN or $5 \times 10^9$ cfu/ml pEcN. Food intake and body weight were measured three times per week and body fat composition and kaolin intake were measured once a week. A glucose tolerance test (OGTT) was performed after the last treatment day.
Figure 19A:
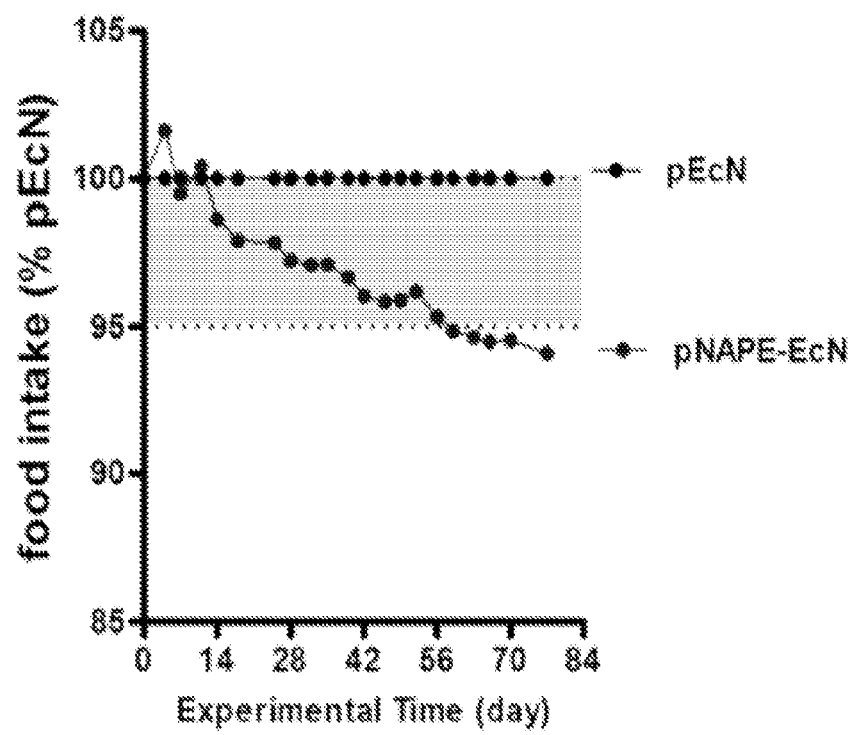
FIG. 19. Mice in which obesity was induced prior to treatment with *E. coli* Nissle 1917 secreting NAPE (pNAPE-EcN) have reduced food intake (A), body weight (B), and adiposity (C) when fed a high-fat diet following a period of treatment. The reduction appears as early as a couple of weeks following initiation of treatment.
Figure 19B:
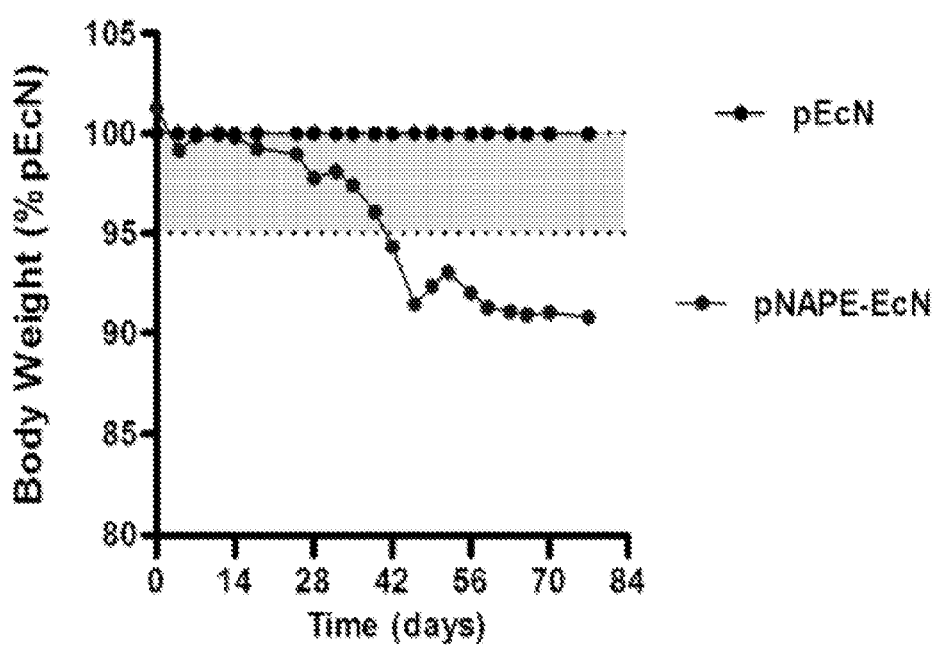
Figure 19C:
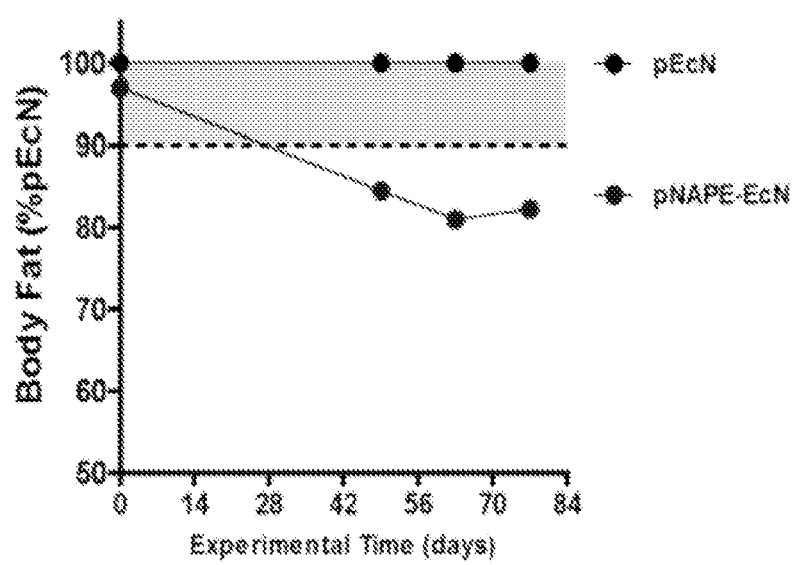

Additional studies were performed with in mice in which obesity was induced prior to treatment. With reference to FIG. 18, mice were given a high fat diet for 9 weeks prior to starting treatment with bacteria. The high fat diet continued at the start of and during treatment, which was continued for 11 weeks. Mice were treated using drinking water supplemented with $5 \times 10^9$ cfu/ml pNAPE-EcN, or $5 \times 10^9$ cfu/ml pEcN. Food intake and body weight were measured three times per week and body fat composition and kaolin intake were measured once a week. An oral glucose tolerance test (OGTT) was performed after the last treatment day. Turning to FIG. 19, treatment of the already obese mice with E. coli Nissle 1917 secreting NAPE (pNAPE-EcN) resulted in reduced food intake, body weight, and adiposity in the mice, even when the high-fat diet was continued. The reduction appears as early as a couple of weeks following initiation of treatment.

Throughout this document, various references are mentioned. All such references are incorporated herein by reference, including the references set forth in the following list:

REFERENCES

1. Harris, K., Kassis, A., Major, G. & Chou, C. J., Is the Gut Microbiota a New Factor Contributing to Obesity and Its Metabolic Disorders? *Journal of Obesity* 2012(2012).
2. Wang, Z., et al. Gut flora metabolism of phosphatidylcholine promotes cardiovascular disease. *Nature* 472, 57-63 (2011).
3. Turnbaugh, P. J., et al. An obesity-associated gut microbiome with increased capacity for energy harvest. *Nature* 444, 1027-1031 (2006).
4. Turnbaugh, P. J., et al. A core gut microbiome in obese and lean twins. *Nature* 457, 480-484 (2009).
5. Vijay-Kumar, M., et al. Metabolic syndrome and altered gut microbiota in mice lacking Toll-like receptor 5. *Science* 328, 228-231 (2010).
6. Cani, P. D., et al. Changes in gut microbiota control metabolic endotoxemia-induced inflammation in high-fat diet-induced obesity and diabetes in mice. *Diabetes* 57, 1470-1481 (2008).
7. Membrez, M., et al. Gut microbiota modulation with norfloxacin and ampicillin enhances glucose tolerance in mice. *FASEB J* 22, 2416-2426 (2008).
8. Fu, J., et al. Food intake regulates oleoylethanolamide formation and degradation in the proximal small intestine. *J Biol Chem* 282, 1518-1528 (2007).
9. Hansen, H. S. & Diep, T. A. N-acylethanolamines, anandamide and food intake. *Biochem Pharmacol* 78, 553-560 (2009).
10. Petersen, G., et al. Intestinal levels of anandamide and oleoylethanolamide in food-deprived rats are regulated through their precursors. *Biochim Biophys Acta* 1761, 143-150; discussion 141-142 (2006).
11. Schwartz, G. J., et al. The lipid messenger OEA links dietary fit intake to satiety. *Cell Metab* 8, 281-288 (2008).
12. Rodriguez de Fonseca, F., et al. An anorexic lipid mediator regulated by feeding. *Nature* 414, 209-212 (2001).
13. Nielsen, M. J., Petersen, G., Astrup, A. & Hansen, H. S. Food intake is inhibited by oral oleoylethanolamide. *J Lipid Res* 45, 1027-1029 (2004).
14. Terrazzino, S., et al. Stearoylethanolamide exerts anorexic effects in mice via down-regulation of liver stearoyl-coenzyme A desaturase-1 mRNA expression. *FASEB J* 18, 1580-1582 (2004).
15. Gillum, M. P., et al. N-acylphosphatidylethanolamine, a gut-derived circulating factor induced by fat ingestion, inhibits food intake. *Cell* 135, 813-824 (2008).
16. Srisai, D., et al. Characterization of the hyperphagic response to dietary fat in the MC4R knockout mouse. *Endocrinology* 152, 890-902 (2011).
17. Guzman, M., et al. Oleoylethanolamide stimulates lipolysis by activating the nuclear receptor peroxisome proliferator-activated receptor alpha (PPAR-alpha). *J Biol Chem* 279, 27849-27854 (2004).
18. Fu, J., Oveisi, F., Gaetani, S., Lin, E. & Piomelli, D. Oleoylethanolamide, an endogenous PPAR-alpha agonist, lowers body weight and hyperlipidemia in obese rats. *Neuropharmacology* 48, 1147-1153 (2005).
19. Fu, J., et al. Oleylethanolamide regulates feeding and body weight through activation of the nuclear receptor PPAR-alpha. *Nature* 425, 90-93 (2003).
20. Lo Verme, J., et al. The nuclear receptor peroxisome proliferator-activated receptor-alpha mediates the anti-inflammatory actions of palmitoylethanolamide. *Mol Pharmacol* 67, 15-19 (2005).

21. Overton, H. A., et al. Deorphanization of a G protein-coupled receptor for oleoylethanolamide and its use in the discovery of small-molecule hypophagic agents. *Cell Metal.* 3, 167-175 (2006).
22. Lauffer, L. M., Iakoubov, R. & Brubaker. P. L. GPR119 Is Essential for Oleoylethanolamide-Induced Glucagon-Like Peptide-1 Secretion From the Intestinal Enteroendocrine L-Cell. *Diabetes* 58, 1058-1066 (2009).
23. Thabuis, C., et al. Lipid transport function is the main target of oral oleoylethanolamide to reduce adiposity in high-fat-fed mice. *J Lipid Res* 52, 1373-1382 (2011).
24. Faure, L., et al. Discovery and characterization of an *Arabidopsis thaliana* N-acylphosphatidylethanolamine synthase. *J Biol Chem* 284, 18734-18741 (2009).
25. Guo, L., Amarnath, V. & Davies, S. S. A liquid chromatography-tandem mass spectrometry method for measurement of N-modified phosphatidylethanolamines. *Anal Biochem* 405, 236-245 (2010).
26. Bulat, E. & Garrett, T. A. Putative N-acylphosphatidy-lethanolamine synthase from *Arabidopsis thaliana* is a lysoglycerophospholipid acyltransferase. *J Biol Chem* 286, 33819-33831 (2011).
27. Horn, C. C., De Jonghe, B. C., Matyas, K. & Norgren, R. Chemotherapy-induced kaolin intake is increased by lesion of the lateral parabrachial nucleus of the rat. *Am J Physiol Regul Integr Comp Physiol* 297, R1375-1382 (2009).
28. Hansen, H. H., Hansen, S. H., Schousboe, A. & Hansen, H. S. Determination of the phospholipid precursor of anandamide and other N-acylethanolamine phospholipids before and after sodium azide-induced toxicity in cultured neocortical neurons. *J Neurochem* 75, 861-871 (2000).
29. Fu, J., Kim, J., Oveisi, F., Astarita, G., and Piomelli, D. (2008) Targeted enhancement of oleoylethanolamide production in proximal small intestine induces across-meal satiety in rats. *Am J Physiol Regul Integr Comp Physiol* 295, R45-50.
30. Jin, X. H., Okamoto, Y., Morishita, J., Tsuboi, K., Tonai, T., and Ueda, N. (2007) Discovery and characterization of a Ca2+-independent phosphatidylethanolamine N-acyl-transferase generating the anandamide precursor and its congeners, *J Biol Chem* 282, 3614-1623.
31. Jin, X. H., Uyama, T., Wang, J., Okamoto, Y., Tonai, T., and Ueda, N. (2009) cDNA cloning and characterization of human and mouse Ca(2+)-independent phosphatidyle-thanolamine N-acyltransferases. *Biochim Biophys Acta* 1791, 32-38.
32. Lo Verme, J., Gaetani, S., Fu. J., Oveisi, F., Burton, K., and Piomelli, D. (2005) Regulation of food intake by oleoylethanolamide, *Cell Mol Life Sci* 62, 708-716.
33. Lionel Faure, Denis Coulon, Jeanny Laroche-Traineau, Marina Le Guedard, Jean-Marie Schmitter, Eric Testet, René Lessire, and Jean-Jacques Bessoule, "Discovery and Characterization of an *Arabidopsis thaliana* N-Acylphos-phatidylethanolamine Synthase" *J. Biol. Chem.* 2009 284: 18734-18741.
34. Uyama, T.; Ikematsu, N.; Inoue, M.; Shinohara, N.; Jin, X-H; Tsuboi, K; Tonai, T.; Tokumura, A.; and Ueda, N. (2012) Generation of N-Acylphosphatidylethanolamine by Members of the Phospholipase A/Acyltransferase (PLA/AT) Family. *Journal of Biological Chemistry* 287, 31905-31919.

---

What is claimed is:

1. A method for treating obesity and/or insulin sensitivity in a subject, comprising:
   administering to the subject
      a bacterium for overexpressing a N-acyl-phosphatidylethanolamine (NAPE); or a compositions comprising a bacterium for overexpressing a N-acyl-phosphatidylethanolamine (NAPE), wherein the bacterium is transfected with a vector comprising a nucleic acid encoding an enzyme for synthesizing NAPE; wherein the enzyme is selected from NAPE acyltransferase and NAPE-phospholipase D (NAPE-PLD); and
      an ingestible vehicle in which the bacterium is provided;
   wherein the vector includes a promoter that can be recognized by endogenous *E. coli* polymerase; and
   wherein the vector includes a T5 promoter.

2. The method of claim 1, wherein the bacterium is capable of colonizing in the gut of the subject.

3. The method of claim 1, wherein the bacterium is an entric bacterium.

4. The method of claim 1, and further comprising administering an antibiotic treatment prior to administering the bacterium.

5. The method of claim 1, wherein the bacterium is administered at least every 12 weeks during a treatment period.

6. The method of claim 1, wherein the NAPE is selected from one or more of the NAPEs in the following group: $C_{16:0}$NAPE, $C_{16:1}$NAPE, $C_{17cy}$NAPE, $C_{18:0}$NAPE, $C_{18:1}$NAPE, and $C_{18:2}$NAPE.

7. The method of claim 1, wherein the bacterium is transfected with one or more vectors comprising nucleic acids encoding at least two enzymes selected from a NAPE acyltransferase, and NAPE-phospholipase D (NAPE-PLD).

8. The method of claim 1, wherein a lac Z operator has been removed.

* * * * *

UNITED STATES PATENT AND TRADEMARK OFFICE
CERTIFICATE OF CORRECTION

| | | |
|---|---|---|
| PATENT NO. | : 9,795,640 B2 | Page 1 of 1 |
| APPLICATION NO. | : 14/345906 | |
| DATED | : October 24, 2017 | |
| INVENTOR(S) | : Davies et al. | |

It is certified that error appears in the above-identified patent and that said Letters Patent is hereby corrected as shown below:

In the Specification

Column 1, Lines 13-18 Replace the second paragraph with the following:
Government Support
This invention was made with government support under grant numbers OD003137, DK059637, DK020593 and RR024975 awarded by the National Institutes of Health. The government has certain rights in the invention.

Signed and Sealed this
Fourth Day of August, 2020

Andrei Iancu
*Director of the United States Patent and Trademark Office*

SEQUENCE LISTING

```
<160> NUMBER OF SEQ ID NOS: 10

<210> SEQ ID NO 1
<211> LENGTH: 861
<212> TYPE: DNA
<213> ORGANISM: Arabidopsis thaliana

<400> SEQUENCE: 1
atggctatgg ggaagataat ggaatgggca gcaagatctg atcatttggg aggaattcca      60
aggaatactg tgataatggc tgttagtgca tttgcaaaag cagtagcaaa tctttgcaat     120
aaaagctcag ttcacaatgc agatactctt atgaatcttg tccagtcaag accacctggt     180
gttcctctca tcactgttag taatcacatg tcgactttgg atgatccagt aatgtggggg     240
gcatttaagg gtctcctttc cttagatcca gaattggctc ggtgggttct tgctgcagag     300
gatatatgtt tcaggaaccc tatattctcc tacattttcc gcactggaaa atgtatacct     360
ataactagag gtggtggaat ctaccaagaa aacatgaatg aagctctcca gcgattaaaa     420
gatggatctt ggctgcatac cttcccagag ggaaaggtgt ttcaagatga tgttcctata     480
agacgactta aatggggaac tgcaagcctc atcgcccgtt ccccagttac cccaatcgtt     540
ttgccaataa ttcaccgtgg ttttgaggag atgatgccgg agaactacaa taatggacga     600
agaccactgg taccgttgcc gaacaaacac cttaaagttg tggttggtga accaattgag     660
tttgatgttc caatgatggt tgagactgct gtcttggact cccgccatgt aacccctcct     720
cttcaagaag tgaaatggcc tgtcctcact tctgctggcc aagtgctaga cgaaactgct     780
cagagacacc tctacatagc tctgtccgag aagattcaat cctccttgga aacattgaga     840
ctcttagcca agcggttgtg a                                               861
```

```
<210> SEQ ID NO 2
<211> LENGTH: 90
<212> TYPE: DNA
<213> ORGANISM: Artificial Sequence
<220> FEATURE:
<223> OTHER INFORMATION: Oligo - Sense

<400> SEQUENCE: 2
tcgtcttcac ctcgagaaat cataaaaaat ttatttgctt tgtgagcgga taacaattat      60
aatagattca atcacacaga attcattaaa                                      90

<210> SEQ ID NO 3
<211> LENGTH: 90
<212> TYPE: DNA
<213> ORGANISM: Artificial Sequence
<220> FEATURE:
<223> OTHER INFORMATION: Oligo - Antisense

<400> SEQUENCE: 3
tttaatgaat tctgtgtgat tgaatctatt ataattgtta tccgctcaca aagcaaataa      60 atttttatg atttctcgag gtgaagacga                                       90

<210> SEQ ID NO 4
<211> LENGTH: 90
<212> TYPE: DNA
<213> ORGANISM: Artificial Sequence
<220> FEATURE:
<223> OTHER INFORMATION: Oligo Sense

<400> SEQUENCE: 4
tcgtcttcac ctcgagaaat cataaaaaat ttatttgctt tcaggaaaat ttttctgtat      60
aatagattca atcacacaga attcattaaa                                      90

<210> SEQ ID NO 5
<211> LENGTH: 90
<212> TYPE: DNA
<213> ORGANISM: Artificial Sequence
<220> FEATURE:
<223> OTHER INFORMATION: Oligo Antisense

<400> SEQUENCE: 5
tttaatgaat tctgtgtgat tgaatctatt atacagaaaa attttcctga aagcaaataa      60 atttttatg atttctcgag gtgaagacga                                       90

<210> SEQ ID NO 6
<211> LENGTH: 31
<212> TYPE: DNA
<213> ORGANISM: Artificial Sequence
<220> FEATURE:
<223> OTHER INFORMATION: Sense

<400> SEQUENCE: 6
cgcggatcca tggctatggg gaagataatg g                                    31

<210> SEQ ID NO 7
<211> LENGTH: 33
<212> TYPE: DNA
<213> ORGANISM: Artificial Sequence
<220> FEATURE:
<223> OTHER INFORMATION: Antisense

<400> SEQUENCE: 7
gagagagctc tcacaaccgc ttggctaaga gtc                                  33
```

```
<210> SEQ ID NO 8
<211> LENGTH: 1191
<212> TYPE: DNA
<213> ORGANISM: Mus musculus

<400> SEQUENCE: 8
atggatgagt atgaggacag ccagtctcca gcgccaagct atcagtatcc aaaagaaaca      60
ctgagaaagc gccagaattc agtgcagaat tcaggaggaa gtgtgtcttc taggttctcc     120
aggaaaagct tcaagctgga ttacagacta gaggaggacg taactaaatc aaagaaagga     180
aaagacggga gatttgttaa cccatggcca acatggaaaa acatctccat cccgaatgtg     240
ctcagatggc tgataatgga gaagaatcac agcggcgttc caggttccaa agaggaactt     300
gacaaagagc tcccggtgct taagccatat tttgtcagtg accctgaaga cgctggagtg     360
agagaggctg gcttacgagt cacgtggctg ggacatgcga cgctgatggt ggaaatggac     420
gagctcatct tcctcacgga ccccatgttc agctcccgtg cctctccctc gcagtacatg     480
ggtccgaagc ggtttcgccg cccgccgtgt acaataagcg aactccccac gatagatgct     540
gtcctcatca gtcacaacca ctacgaccac ctagactacg gctcggtcct ggcgttgaac     600
gagcggttcg gcagcgagct gcggtggttt gtgcccttgg gccttcttga ctggatgcag     660
aaatgtggct gcgagaacgt gattgagctg gactggtggg aggagaactg cgtccctggc     720
cacgacaagg tcaccttcgt cttcacgcct tcccagcact ggtgcaaaag gaccctcctg     780
gacgacaaca aggttctctg gggcagctgg tccgtgctag ggccttggag tcgattcttc     840
tttgctgggg atactggcta ctgccccgct tttgaagaga ttggaaaaag gtttggtcct     900
tttgaccttg cggccattcc catcggagct tatgaaccaa ggtggtttat gaaataccag     960
catgcagacc cagaagatgc tgtaaggatt cacattgacc ttcaaacaaa gagatctgtg    1020
gcgattcact gggggacgtt tgccttagct aatgagcatt acctagagcc gccagtgaaa    1080
ctgaatgaag ctctagagag atacggactt tcttgtgagg atttcttcat actgaagcat    1140
ggagagtcga gatacttgaa taccgatgat agagcttttg aagaaacatg a             1191

<210> SEQ ID NO 9
<211> LENGTH: 33
<212> TYPE: DNA
<213> ORGANISM: Artificial Sequence
<220> FEATURE:
<223> OTHER INFORMATION: sense

<400> SEQUENCE: 9
cgcggatcca tggatgagta tgaggacagc cag                                    33

<210> SEQ ID NO 10
<211> LENGTH: 39
<212> TYPE: DNA
<213> ORGANISM: Artificial Sequence
<220> FEATURE:
<223> OTHER INFORMATION: Antisense

<400> SEQUENCE: 10
gagagatatc tcatgtttct tcaaaagctc tatcatcgg                              39
```